(12) United States Patent
Arnoult et al.

(10) Patent No.: US 8,758,746 B2
(45) Date of Patent: Jun. 24, 2014

(54) FERTILIZATION MODULATION COMPOUNDS AND PROCESS FOR IMPLEMENTING THEM

(75) Inventors: Christophe Arnoult, Saint Etienne de Crossey (FR); Michel De Waard, Saint Christophe sur Guiers (FR); Gerard Lambeau, Grasse (FR)

(73) Assignees: Universite Joseph Fourier, Grenoble (FR); Centre National de la Recherche Scientifique, Paris (FR)

( * ) Notice: Subject to any disclaimer, the term of this patent is extended or adjusted under 35 U.S.C. 154(b) by 41 days.

(21) Appl. No.: 13/259,579

(22) PCT Filed: Mar. 24, 2010

(86) PCT No.: PCT/EP2010/053815
§ 371 (c)(1),
(2), (4) Date: Oct. 27, 2011

(87) PCT Pub. No.: WO2010/108942
PCT Pub. Date: Sep. 30, 2010

(65) Prior Publication Data
US 2012/0034204 A1 Feb. 9, 2012

(30) Foreign Application Priority Data
Mar. 24, 2009 (EP) .................................... 09305261

(51) Int. Cl.
*A61K 38/46* (2006.01)

(52) U.S. Cl.
USPC ................................ 424/94.6; 435/2; 435/325

(58) Field of Classification Search
CPC ..... A61K 38/46; A61K 38/465; C12N 5/076; C12N 15/111; A61P 15/08
See application file for complete search history.

(56) References Cited

U.S. PATENT DOCUMENTS

| 2003/0073087 A1 | 4/2003 | Lazdunski et al. |
| 2007/0128179 A1 | 6/2007 | Gopalakrishnakone et al. |

FOREIGN PATENT DOCUMENTS

| WO | 0159129 A2 | 8/2001 |
| WO | 0231127 A2 | 4/2002 |

OTHER PUBLICATIONS

Kyono K. et al., Effects of Phospholipase Az, Lysophosphatidyl Choline, and Fatty Acid on the Acrosome Reaction of Human Spermatozoa, Tohoku J. Exp. Med., 1984, vol. 144, pp. 257-563.*
Lachapelle M-H. et al., Effect of lysoplatelet-activating factor on human sperm fertilizing ability, Fertility and Sterility, 1993, vol. 59, No. 4, pp. 863-863.*
Riffo M. S. et al ., Role of Phospholipase A2 in Mammalian Sperm-Egg Fusion: Development of Hamster Oolemma Fusibility by Lysophosphatidylcholine, The Journal of Experimental Zoology, 1997, vol. 279, pp. 81-88.*
Singer A.G. et al., Interfacial Kinetic and Binding Properties of the Complete Set of Human and Mouse Groups I, II, V, X, and XII Secreted Phospholipases A2, The Journal of Biological Chemistry, 2002, vol. 277, No. 50, pp. 48535-48549.*
Escoffier J. et al., "Group X Secreted Phospholipase A2 Specifically Decreases Sperm Motility in Mice", Journal of Cellular Physiology, 2011 (published online on Dec. 28, 2010), vol. 226, pp. 2601-2609.*
E. Baldi et al: "Intracellular Events and Signaling Pathways Involved in Sperm Aquisition of Fertilizing Capacity and Acrosome Reaction", Frontiers in Bioscience, vol. 5, Nov. 1, 2000, pp. E110-E123.
J. Lessig et al: "Destabilization of the acrosome results in release of phospholipase A2 from human spermatozoa and subsequent formation of lysophospholipids", Andrologia, vol. 38, 2006, pp. 69-75.
L.T. Budnik et al: "Lysophosphatidic acid and its Role in Reproduction", Biology of Reproduction, vol. 66, 2002, pp. 859-865.
E. R. S. Roldan et al: "Sperm phospholipases and acrosomal exocytosis", Frontiers in Bioscience, vol. 12, Jan. 1, 2007, pp. 89-104.
International Search Report, dated May 7, 2010, in PCT/EP2010/053815.
European Search Report, dated Oct. 30, 2009, in EP 09305261.

* cited by examiner

*Primary Examiner* — Satyendra Singh
(74) *Attorney, Agent, or Firm* — Young & Thompson

(57) ABSTRACT

This invention relates to fertilization modulation compounds and process for implementing them.

7 Claims, 11 Drawing Sheets

FERTILIZATION MODULATION COMPOUNDS AND PROCESS FOR IMPLEMENTING THEM

This invention relates to fertilization modulation compounds and process for implementing them.

Secreted phospholipases A2 (sPLA2s) have been first described in animal venoms. In snake venoms, sPLA2s are usually the most important compound in weight and one snake venom can contain up to 15 different sPLA2s. These enzymes play crucial roles in venom toxicity and are responsible for a wide range of toxic effects like neurotoxic, cardiotoxic or cytotoxic effects. All sPLA2s present in one venom do not show the same enzymatic properties and each sPLA2 presents a specific pattern of toxicity. By sequence homology, many sPLA2s have been cloned in Mammals (Valentin and Lambeau, 2000; What can venom phospholipases A(2) tell us about the functional diversity of Mammalian secreted phospholipases A(2)? *Biochimie.* 82:815-831). Phospholipase A2 (PLA2) is now a large family of enzymes and have been split in four groups, depending on calcium sensitivity and cellular localization: the secreted PLA2 (sPLA2), the cellular PLA2 (cPLA2), both calcium dependent, and two calcium independent groups (iPLA2 and PAF acetylhydrolase).

If one focuses on secreted PLA2s, ten different genes have been described in mouse so far, corresponding to the groups of IB-, IIA-, IIC-, IID-, IIE-, IIF-, III-, V-, X- and XIIA-sPLA2. For comparison, venom sPLA2s either belong to group I (elapid and hydrophid snakes) or group II (viperid and crotalid snakes). Concerning the enzymatic activity, the sPLA2 family is characterized by its ability to hydrolyse the sn-2 ester of glycero-phospholipids of the extracellular leaflet of the plasma membrane in two components, a fatty acid (FA) and a lysophospholipid (LysoPL). Both of these compounds have the ability to leave the plasma membrane. Because FAs rapidly equilibrate between both leaflets of the membrane bilayer, they diffuse into the cytoplasm and control different cellular signalling pathways as second messengers. By contrast, LysoPLs accumulate in the outer leaflet.

However, the lysophospholipid contains a glycerophosphate polar head group and a more lipophilic fatty acid group (in position 1 on the glycerol). Depending on the fatty acid nature, the lysophospholipid will partition between the plasma membrane and the aqueous phase and may act as a bioactive metabolite in different extracellular pathways in an autocrine or paracrine mode.

Studies have shown that the mammalian sPLA2 enzymes are widely expressed in numerous tissues and organs but their cellular roles in cell physiology remain largely unknown (Lambeau and Gelb, 2008, Biochemistry and physiology of Mammalian secreted phospholipases A2. *Annu. Rev. Biochem.* 77:495-520. What can venom phospholipases A(2) tell us about the functional diversity of Mammalian secreted phospholipases A(2)? *Biochimie.* 82:815-831.).

In male reproductive organs, a wide range of different types of sPLA2 have been described. Mature sperm cells, epididymis, vas deferens and seminal vesicle express IIC-, IID-, IIE-, IIF-, V- and X-sPLA2; prostate expresses IIC-, IID-, IIE- and IIF-sPLA2 (Masuda, Murakami, Matsumoto, Eguchi, Urade, Lambeau, Gelb, Ishikawa, Ishii, and Kudo, 2004, Localization of various secretory phospholipase A2 enzymes in male reproductive organs. *Biochim. Biophys. Acta.* 1686:61-76). The reasons for such a diversity of sPLA2s expression in the different compartments of the genital male organs, and their specific cellular functions are unknown so far.

The presence of sPLA2 in epididymis, seminal vesicle and prostate may explain the presence of PLA2 activity in the seminal plasma of ejaculated sperm (Kallajoki, Alanen, Nevalainen, and Nevalainen, 1998, Group II phospholipase A2 in human male reproductive organs and genital tumours. *Prostate.* 35:263-272). Currently, the roles of sPLA2 in seminal plasma are not well understood: these enzymes may participate in host defense of the male tracts because of a strong antibacterial activity of some sPLA2s. However, secreted PLA2s released by the different cell types of the reproductive male organs may also control different key events of sperm physiology in female tract like capacitation, sperm motility or acrosome reaction (AR).

Finally, the presence of strong inhibitors of sPLA2 enzymatic activity in the same seminal plasma (Manjunath, Soubeyrand, Chandonnet, and Roberts, 1994; Major proteins of bovine seminal plasma inhibit phospholipase A2. *Biochem. J.* 303:121-128; Upreti, Hall, Koppens, Oliver, and Vishwanath, 1999, Studies on the measurement of phospholipase A2 (PLA2) and PLA2 inhibitor activities in ram semen. *Anim Reprod. Sci.* 56:107-121) puzzles a little bit more the presence of these enzymes and their physiological roles in seminal plasma.

In sperm cell, lipid metabolism is central for sperm physiology. Modifications of phospholipids by phospholipases (PL) belonging to different families are involved in different crucial steps of sperm physiology (reviewed by (Roldan and Shi, 2007, Sperm phospholipases and acrosomal exocytosis. *Front Biosci.* 12:89-104). For instance, lipid plasma membrane composition plays critical roles in sperm physiology. The lipid composition changes during sperm capacitation and the main event characterizing this evolution is an efflux of cholesterol activated by calcium and bicarbonate influx (Visconti, Ning, Fornes, Alvarez, Stein, Connors, and Kopf, 1999, Cholesterol efflux-mediated signal transduction in Mammalian sperm: cholesterol release signals an increase in protein tyrosine phosphorylation during mouse sperm capacitation. *Dev. Biol.* 214:429-443). The decrease of cholesterol concentration in plasma membrane is thus a priming step necessary for acrosome reaction. AR is also controlled by phospholipids metabolism: for instance Phospholipase C (PLC) plays a crucial role in the calcium signalling of this exocytotic event (O'Toole, Arnoult, Darszon, Steinhardt, and Florman, 2000, Ca(2+) entry through store-operated channels in mouse sperm is initiated by egg ZP3 and drives the acrosome reaction. *Mol. Biol. Cell* 11:1571-1584). Concerning sPLA2, group IIE, V and X have been interestingly localized in the acrosomal zone of spermatids (Masuda, Murakami, Matsumoto, Eguchi, Urade, Lambeau, Gelb, Ishikawa, Ishii, and Kudo, 2004, Localization of various secretory phospholipase A2 enzymes in male reproductive organs. *Biochim. Biophys. Acta.* 1686:61-76).

Although there are no data linking sPLA2 and AR, several observations strongly suggest that an uncharacterized and endogenous PLA2 plays an important role in the exocytotic event.

Indeed, there are several indirect proofs for the involvement of sPLA2 during this exocytotic even. For instance, inhibitors of PLA2, like mepacrine or 4-bromophenacyl bromide (BPB) block the calcium-ionophore induced acrosome reaction (Roldan and Fragio, 1993, Phospholipase A2 activation and subsequent exocytosis in the Ca2+/ionophore-induced acrosome reaction of ram spermatozoa. *J. Biol. Chem.* 268:13962-13970; Llanos, Morales, and Riffo, 1993, Studies of lysophospholipids related to the hamster sperm acrosome reaction in vitro. *J. Exp. Zool.* 267:209-216).

Moreover, the two products of sPLA2 enzymatic activity (lysophospholipids and/or fatty acids) accelerate or promote exocytosis (Fleming and Yanagimachi, 1984, Evidence suggesting the importance of fatty acids and the fatty acid moieties of sperm membrane phospholipids in the acrosome reaction of guinea pig spermatozoa. *J. Exp. Zool.* 229:485-489; Llanos, Morales, and Riffo, 1993, Studies of lysophospholipids related to the hamster sperm acrosome reaction in vitro. *J. Exp. Zool.* 267:209-216).

Finally, zona pellucida-induced acrosome reaction leads to a concomitant release of lipid metabolites, a hint of an PLA2 activation (Yuan, Chen, Shi, Mao, Yu, Fang, and Roldan, 2003, Zona pellucida induces activation of phospholipase A2 during acrosomal exocytosis in guinea pig spermatozoa. *Biol. Reprod.* 68:904-913). In this context, what roles play the different sPLA2 present in the sperm environment, an even likely localized inside the sperm cell in the acrosome? This question is still a matter of debate and only hypotheses were proposed. For instance, sperm sPLA2 may act in a paracrine or exocrine way to control sperm physiology.

In order to better understand the specific roles of all these enzymes, different genetically modified null mice for mouse group V (mGV) and mouse group X (mGX) sPLA2 genes have been produced (Henderson, Jr., Chi, Bollinger, Tien, Ye, Castelli, Rubtsov, Singer, Chiang, Nevalainen, Rudensky, and Gelb, 2007, Importance of group X-secreted phospholipase A2 in allergen-induced airway inflammation and remodelling in a mouse asthma model. *J. Exp. Med.* 204:865-877; Satake, Diaz, Balestrieri, Lam, Kanaoka, Grusby, and Arm, 2004, Role of group V phospholipase A2 in zymosan-induced eicosanoid generation and vascular permeability revealed by targeted gene disruption. *J. Biol. Chem.* 279:16488-16494). Moreover, in the C57BL/6 strain mice, the mGIIA-sPLA2 is naturally disrupted (Kennedy, Payette, Mudgett, Vadas, Pruzanski, Kwan, Tang, Rancourt, and Cromlish, 1995, A natural disruption of the secretory group II phospholipase A2 gene in inbred mouse strains. *J. Biol. Chem.* 270:22378-22385). No major male reproductive defects have been described in all of these strains so far, and thus these transgenic mouse strains did not give any indications or information concerning the specific roles of these three enzymes in sperm physiology, which remain to be analyzed by more specialized experiments. The presence of different sPLA2s, possibly acting as redundant enzymes, may explain the lack of phenotypes.

Beside their ability to hydrolyze phospholipids, sPLA2 are also ligands for different types of membrane receptors. So far, two different receptors have been characterized using snake venom sPLA2 as ligands: the M-Receptor in skeletal muscles and the N-receptor in neurons. The affinity of sPLA2 for these receptors is remarkably high, and some snake sPLA2s bind to these both receptors with affinities lower than 10 picoM. Some mammalian sPLA2s bind also with a very high affinity to these receptors. However, the physiological relevance of such a binding is still not understood in the context of cellular physiology. Interestingly, the M-type receptor belongs to the C-type lectin superfamily, sugar binding proteins. It is known that lectins play a peculiar role in sperm physiology since sperm acrosome reaction depends on the species-specific carbohydrate moiety of ZP3, a glycoprotein known to be central in the sperm-oocyte binding event.

Fertilization is an essential step for the reproduction and must be improved in some cases.

Promotion or improvement of the fertilization is used for instance for the reproduction of animal varieties, in particular during the assisted reproductive technology (ART) for improving bovine, ovine or caprine varieties.

Treatment of Mammal sterility, in particular human sterility can be carried out in vivo or in vitro and in particular during the assisted reproductive technology (ART).

Assisted reproductive technology in Mammals is based in particular on mixing of spermatozoa and oocytes which lead by fusion to embryos. Embryos are then transferred in the female tract. The success rate is 50% of embryos obtained compared to the number of oocytes harvested (data obtained for IVF in human, France 2005). After transfer of the embryos in uterus, the success rate highly decreases and only one of ten embryos transferred will lead to birth.

Therefore, there is a need for improving the final fertilization rate, by promoting the yield of viable embryos.

Furthermore, fertilization modulation and in particular assisted reproductive technology are associated with an increased risk of birth defects.

One of the aims of the invention is to provide compounds and derivatives thereof and their use for the treatment of sterility or for promoting or improving the fertilization, in particular during assisted reproduction technology allowing to obtain an improved spermatozoon maturation and an improved fertilization rate and promoting the embryogenesis, in particular viable embryogenesis and without presenting genetic anomaly.

Another aim of the invention is to provide compounds and derivatives thereof and their use for the prevention of the fertilization.

Still another aim is to provide pharmaceutical compositions for the promotion and/or the improvement of fertilization, or the prevention of fertilization.

Another aim of the invention is to provide a process for the treatment of sterility or for promoting or improving fertilization.

Another aim of the invention is to provide a process of selection of spermatozoa.

Still another aim of the invention is to provide a process to diagnostic infertility in a Mammal.

Another aim of the invention is to provide a contraception process.

The present invention relates to the use of secreted phospholipase A2 (sPLA2) and/or at least one metabolite produced by said sPLA$_2$ liable to modulate the fertilization, for the manufacture of an anti sterility drug, or of a fertilization promoting or improving drug, or of a viable embryogenesis promoting or improving drug, or of a contraceptive drug.

The present invention results from pointing out an unexpected function of sPLA2 itself or of its metabolites enabling to target inefficient spermatozoa (with respect to fertilization) and thus possibly to discard them, without negative impact on efficient spermatozoa, said function of sPLA2 itself or of its metabolites being involved on sperm acrosome reaction (AR), even in the absence of oocytes, and before the normal AR occurs.

The sPLA2 itself or of its metabolites treatment thus triggers an early AR in the absence of oocytes, i.e. a targeted AR, on a particular population of sperms, in particular on inefficient sperms, allowing selecting efficient sperms from inefficient sperms.

AR is the reaction that occurs in the acrosome of the sperm as it binds to the coating layer of egg that is the zona pellucida of the egg. AR is an exocytotic event allowing the release of enzymes required to destroy locally the zona pellucida proteins.

By the term "metabolite", it must be understood the product formed by the hydrolysis of the sn-2 ester glycero-phospholipids with sPLA$_2$.

The metabolites produced by the hydrolysis of the sn-2 ester glycero-phospholipids can be arachidonic acid, myristoleic acid, palmitoleic acid, sapienic acid, oleic acid, linoleic acid, α-linolenic acid, eicosapentaenoic acid, docosahexaenoic acid, lysophosphatidylcholine, lysophosphatidylethanolamine, lysophosphatidylserine, lysophosphatidylinositol, lysophosphatidylglycerol or lysophosphatidate.

The term "to modulate" means to adjust or adapt to a certain proportion; or to regulate or stimulate.

According to the Cambridge Advanced Learner's Dictionary, (3rd Edition, Cambridge University Press), the term "fertilize" means: "to cause an egg or seed to start to develop into a new young animal or plant by joining it with a male cell"

Therefore, the term "fertilization" in this specification means the process by which egg cells of a Mammal are joined with sperm, i.e. from gathering the sperm with oocytes in a same medium to the recovery of multicellular embryos before implantation, comprising the fusion of an ovum with a spermatozoon, and obtaining an embryo at the stage "two-cells".

Therefore, the expression "modulate the fertilization" means that the fertilization in a Mammal can be increased:
compared to the one of a healthy Mammal, or
compared to the own level of fertilization of said Mammal, i.e. the yield rate of the Mammal has been increased.

The increase of the fertilization can be shown with an IVF test such as the one used in example 7 (L. Fraser, (1993) In vitro capacitation and fertilization p239-263 in Methods in Enzymology, vol 225).

In the rest of this specification, the terms spermatozoa, spermatozoon(s) and sperm(s) will be used independently and will have the same meaning.

Sterility in a human and therefore in a Mammal, and in particular in a woman (also designated by infertility) is often defined as the impossibility to get pregnant after trying so for one year. Thus, one of the advantages of the invention is to provide a drug treating the sterility and thus helping a Mammal to become pregnant. In this case, the modulation of the fertilization is an increase of the fertilization.

By "fertilization promoting drug", it must be understood a drug enabling the fertilization in cases in which it would be impossible. Therefore, another advantage of the invention is to provide a drug able to obtain viable embryos, i.e. to obtain a fertilization level of a Mammal, in particular a human close to the one of a healthy Mammal.

In this case, the modulation of the fertilization is also an increase of the fertilization.

By "fertilization improving drug", it must be understood a drug able to ameliorate, enhance, increase or boost the fertilization. Therefore, another advantage of the invention is to provide a drug able to obtain a fertilization level of a Mammal higher the one of a healthy Mammal.

In this case, the modulation of the fertilization is also an increase of the fertilization.

By "viable embryogenesis promoting drug" it must be understood a drug able not only to promote the fertilization but also to lead to a viable embryo, at least constituted of two cells.

By "viable embryogenesis improving drug" it must be understood a drug able not only to improve the fertilization but also to lead to one or more viable embryos, at least constituted of two cells, and advantageously enabling to get a new healthy born Mammal able to develop into a healthy Mammal.

A viable embryo is defined by an embryo which has a normal development up to the blastocyte stage before implantation and up to new born stage after implantation (Methods in enzymology, vol 255).

It must be specified that the modulation of the fertilization concerns:
either a human population wherein the fertilization rate is increased,
either a human individual wherein the fertilization is made possible
or an animal wherein an increase of the reproduction is required to increase, for instance, but without being limited to, the number of animals, the meat ratio, the quality of meat, the milk production . . . .

The expression "modulation of fertilization" also means also that the fertilization in a Mammal can be decreased or even inhibited.

By "contraceptive drug" is must be understood a drug able to diminish, lower, reduce or even prevent or stop the fertilization in order to lead to a birth controlling drug.

To modulate the fertilization, it must be noted that the sPLA2 used must be active, i.e. able to hydrolyze the sn-2 ester glycero-phospholipids of the extracellular leaflet of the plasma membrane (Singer et al. (2002) Interfacial Kinetic and Binding Properties of the Complete Set of Human and Mouse Groups I, II, V, X, and XII Secreted Phospholipases A2, Journal of Biological Chemistry, 277, 48535-48549).

In an advantageous embodiment, the invention relates to the use of secreted phospholipase A2 (sPLA2) and/or at least one metabolite produced by said $sPLA_2$ as defined above, liable to increase said fertilization for the manufacture of an anti sterility drug, or of a fertilization promoting or improving drug, or of a viable embryogenesis promoting or improving drug.

Thus, in this embodiment, the modulation of the fertilization is an increase of the fertilization.

In an advantageous embodiment, the invention relates to the use of secreted phospholipase A2 (sPLA2) and/or at least one metabolite produced by said $sPLA_2$ as defined above, for a female Mammal undergoing in vitro fertilization (IVF), gamete intrafallopian transfer procedure (GIFT), intracytoplasmic sperm injection (ICSI), or therapeutic donor insemination (TDI), during assisted reproductive technologies (ART).

Assisted reproductive technologies (ART) include all fertility treatments in which both eggs and sperm are handled. In general, ART procedures involve surgically removing eggs from a Mammal's ovaries or female tract, combining them with sperm in the laboratory and transferring back them to the Mammal's body or donating them to another Mammal.

Examples of ART comprise:
in vitro fertilization (IVF) that consists in fertilization of an egg cell of a Mammal by sperm outside the womb, by letting sperm fertilize the egg cell in a fluid medium and transferring the fertilized egg into the female tract of the Mammal,
gamete intrafallopian transfer procedure (GIFT), wherein a mixture of sperm and eggs is placed directly into a Mammal's fallopian tubes using laparoscopy following a transvaginal ovum retrieval,
intracytoplasmic sperm injection (ICSI), wherein a single sperm is carefully injected into the center of an egg using a microneedle,
therapeutic donor insemination (TDI), wherein artificial insemination using donor sperm or, more commonly, donor insemination is carried out.

In a preferred embodiment, the present invention relates to the use of secreted phospholipase A2 (sPLA2) and at least one metabolite produced by said sPLA$_2$ liable to modulate the fertilization, for the manufacture of an anti sterility drug, or of a fertilization promoting or improving drug, or of a viable embryogenesis promoting or improving drug, or of a contraceptive drug.

In a preferred embodiment, the present invention relates to the use of secreted phospholipase A2 (sPLA2) liable to modulate the fertilization, for the manufacture of an anti sterility drug, or of a fertilization promoting or improving drug, or of a viable embryogenesis promoting or improving drug, or of a contraceptive drug.

In a preferred embodiment, the present invention relates to the use of at least one metabolite produced by said sPLA$_2$ liable to modulate the fertilization, for the manufacture of an anti sterility drug, or of a fertilization promoting or improving drug, or of a viable embryogenesis promoting or improving drug, or of a contraceptive drug.

In an advantageous embodiment, the sPLA2 used above presents the property to hydrolyse the sn-2 ester of one or more glycero-phospholipids with a specific activity comprised from about 1 µmol/min/mg to about 50 µmol/min/mg, in particular from about 1 µmol/min/mg to about 25 µmol/min/mg on anionic and zwitterionic glycero-phospholipids.

The "specific activity" of an enzyme is the amount of product formed by the reaction of a substrate with an enzyme in a period of time under given conditions per milligram of enzyme, and thus a measure of enzyme processivity.

sPLA2 has various glycero-phospholipids as substrates and the specific activity of sPLA towards glycero-phospholipids can be determined as in Singer et al. (Interfacial Kinetic and Binding Properties of the Complete Set of Human and Mouse Groups I, II, V, X, and XII Secreted Phospholipases A2, Journal of Biological Chemistry, Vol. 277, No. 50, Issue of December 13, pp. 48535-48549, 2002).

As already discussed above, in sperm cells, lipid metabolism is central for sperm physiology. Modification of phospholipids by phospholipases (PL) belonging to different families are involved in different crucial steps of sperm physiology.

The expression "anionic phospholipids" represents, for example, the cardiolipine, the phosphatidylserine, the phosphatidic acid, the phosphatidylinositol, the phosphatidylglycerol.

The expression "zwitterionic phospholipids" represents, for example, the phosphatidyl choline, the sphingomyeline and the phosphatidyl ethanolamine.

Thus, from about 1 µmol/min/mg to about 50 µmol/min/mg, only a part of the glycerol-phospholipids present in a spermatozoon is hydrolyzed, leading thus to spermatozoa able to give a fertilization rate higher than the one of non-treated spermatozoa.

Below 1 µmol/min/mg, the specific activity is too low to obtain a hydrolysis of phospholipids and thus sPLA2 cannot be involved in said crucial steps of sperm physiology.

Above 50 µmol/min/mg, the specific activity is too high, leading to too high a level of hydrolysis of the glycerol-phospholipids present in a spermatozoon and thus the destruction of sperm cells.

Preferably, in the present invention, "the specific activity of sPLA2 is comprised from about 1 to about 50 µmol/min/mg, in particular from about 1 µmol/min/mg to about 25 µmol/min/mg" is towards one, two, three, four or five glycero-phospholipids, and more preferably towards one, two or three glycero-phospholipids.

In particular, "the specific activity of sPLA2 comprised from about 1 to about 50 µmol/min/mg, in particular from about 1 µmol/min/mg to about 25 µmol/min/mg" is towards one glycero-phospholipids.

More particularly, "the specific activity of sPLA2 comprised from about 1 to about 50 µmol/min/mg, in particular from about 1 µmol/min/mg to about 25 µmol/min/mg" is towards two glycero-phospholipids.

In this embodiment, the specific activity of sPLA2 can be from about 1 to about 50 µmol/min/mg towards a first glycero-phospholipid and from about 1 µmol/min/mg to about 25 µmol/min/mg towards a second glycero-phospholipid, but it can also be from about 1 µmol/min/mg to about 25 µmol/min/mg towards both glycero-phospholipids or from about 1 to about 50 µmol/min/mg towards both glycero-phospholipids.

In particular, "the specific activity of sPLA2 comprised from about 1 to about 50 µmol/min/mg, in particular from about 1 µmol/min/mg to about 25 µmol/min/mg" is towards three glycero-phospholipids.

In this embodiment, the specific activity of sPLA2 can be comprised:
  from about 1 µmol/min/mg to about 50 µmol/min/mg towards three glycero-phospholipids or,
  from about 1 µmol/min/mg to about 50 µmol/min/mg towards one glycero-phospholipid and from about 1 µmol/min/mg to about 25 µmol/min/mg towards two other glycero-phospholipids, or
  from about 1 µmol/min/mg to about 50 µmol/min/mg towards two glycero-phospholipids and about 1 µmol/min/mg to about 25 µmol/min/mg towards a third glycero-phospholipids or, it can also be from about 1 µmol/min/mg to about 25 µmol/min/mg towards three glycero-phospholipids.

In an advantageous embodiment, the sPLA2 used above is a protein of a Mammalian origin, in particular selected from Groups IIA IIF, III, V or X sPLA2, more particularly mouse GX or human GV or human GX, or of prokaryotic origin such as bacterial origin, plant origin, or of other origins including for instance animal venoms, in particular selected from arthropod or snake venoms, more particularly *Apis* spp, *Oxyuranus* spp and *Daboia* spp., or an homologous protein thereof produced as a recombinant protein.

By "Mammalian origins" is meant a class of vertebrate animals (Mammals) giving birth to live young.

The Mammals are divided into two subclasses, the Prototheria, and the Theria, which includes the live-bearing Marsupials and Placentals. Most Mammals, including the six largest orders, belong to the placental group. The three largest orders, in descending order, are Rodentia (mice, rats, and other small, gnawing Mammals), Chiroptera (bats), and Soricomorpha (shrews, moles and solenodons). The next three largest orders include the Carnivora (dogs, cats, weasels, bears, seals, and their relatives), the Cetartiodactyla (including the even-toed hoofed Mammals and the whales) and the Primates to which the Human species belongs.

By "prokaryotic origin" is meant are a group of organisms that lack a cell nucleus (karyon), or any other membrane-bound organelles.

The Prokaryotes are divided into two domains: the Bacteria and the Archaea.

Examples of plant origins, but without being limited to, can be found in Mansfeld J, Ulbrich-Hofmann R. (2007) Secretory phospholipase A2-alpha from *Arabidopsis thaliana*: functional parameters and substrate preference. Chem Phys Lipids. 150:156-66 and Fujikawa R, Fujikawa Y, Iijima N, Esaka M. (2005) Molecular cloning, expression, and characterization of secretory phospholipase A2 in tobacco. Lipids. 40:901-8.

In the present specification, it must be noted that the terms "GX" and "GV" designate sPLA2 from groups X and V respectively.

sPLA2 from groups I, II, V and X are defined in Singer et al. (Interfacial Kinetic and Binding Properties of the Complete Set of Human and Mouse Groups I, II, V, X, and XII Secreted Phospholipases A2, Journal of Biological Chemistry, Vol. 277, No. 50, Issue of December 13, pp. 48535-48549, 2002).

sPLA2 from group III is defined in Sato H, Kato R, Isogai Y, Saka G, Ohtsuki M, Taketomi Y, Yamamoto K, Tsutsumi K, Yamada J, Masuda S, Ishikawa Y, Ishii T, Kobayashi T, Ikeda K, Taguchi R, Hatakeyama S, Hara S, Kudo I, Itabe H, Murakami M. (2008) and Mounier C M, Wendum D, Greenspan E, Fléjou J F, Rosenberg D W, Lambeau G. (2008) Distinct expression pattern of the full set of secreted phospholipases A2 in human colorectal adenocarcinomas: sPLA2-III as a biomarker candidate. Br J Cancer. 98:587-95

Analyses of group III secreted phospholipase A2 transgenic mice reveal potential participation of this enzyme in plasma lipoprotein modification, macrophage foam cell formation, and atherosclerosis. J Biol Chem. 283: 33483-97.

Active sPLA2 isoforms of sPLA2 of various origins above defined can also be used in the present invention.

There are several types of animal venoms, in particular:

neurotoxins that act on the victim's nervous system, causing excitation (cramps, vomiting, convulsions) or depression (paralysis, respiratory or cardiac depression or arrest), hemotoxins that break down the victim's tissues, usually by an acid or a toxin that prevents or causes blood clotting, or destroys red or white blood cells.

Venom usually contains both types, but one dominates.

Enzymes are another important component in animal venoms.

Arthropods are animals belonging to the Phylum Arthropoda and include the insects, arachnids, crustaceans, and others.

Many major groups of animals contain venomous species, including various insects, fish, lizards, scorpions, snakes, and spiders.

*Apis* spp are insects from the Apidae family.

*Oxyuranus* spp are snakes of the Elapidae family found in Australia.

*Daboia* spp are snakes from the Viperidae family found in particular in South East Asia.

In an advantageous embodiment, the sPLA2 above defined purified from the different organisms.

In another preferred embodiment, the sPLA2 is used without purification.

sPLA2 from Mammal, Bacterial or plant origins compared to the one of animal venom origin are preferred to increase the fertilization but a modified sPLA2 of animal venom can also be used to increase the fertilization.

In an advantageous embodiment, glycero-phospholipids hydrolyzed by the sPLA2 above defined are selected from the list consisting of: 1-palmitoyl-2-oleoyl-sn-glycero-3-phosphoglycerol (POPG), 1-palmitoyl-2-oleoyl-sn-glycero-3-phosphocholine (POPC), 1-palmitoyl-2-oleoyl-sn-glycero-3-phosphoserine (POPS).

The glycerol-phospholipids above defined are constituents of the spermatozoon membrane, the proportions of which can differ between subjects.

In another advantageous embodiment, the specific activity of sPLA2 above defined towards POPC is comprised from about 1 to about 25 µmol/min/mg, particularly from about 5 to about 15 µmol/min/mg, more particularly from about 5 to about 10 µmol/min/mg, in particular about 7 µmol/min/mg, and/or the specific activity of sPLA2 towards POPG is comprised from 1 to 50 µmol/min/mg, particularly from about 10 to about 40 µmol/min/mg, more particularly from about 25 to about 35 µmol/min/mg, in particular 30 µmol/min/mg, and/or the specific activity of sPLA2 towards POPS in comprised from about 1 to about 50 µmol/min/mg, particularly from about 10 to about 40 µmol/min/mg, more particularly from about 15 to about 25 µmol/min/mg, in particular about 20 µmol/min/mg.

The specific activity of sPLA2 towards POPG, POPS and POPC can be found in Singer et al. (Interfacial Kinetic and Binding Properties of the Complete Set of Human and Mouse Groups I, II, V, X, and XII Secreted Phospholipases A2, Journal of Biological Chemistry, Vol. 277, No. 50, Issue of December 13, pp. 48535-48549, 2002).

In another advantageous embodiment, sPLA2 above defined is used at a concentration from about 0.2 nM to about 200 nM, preferably from about 0.2 nM to about 20 nM, more preferably from 0.2 to 2 nM, more preferably from about 2 nM to about 200 nM, more preferably from about 2 nM to about 20 nM, more preferably from about 20 nM to about 200 nM, in particular about 200 nM.

As shown in example 5 (a and b) and FIGS. 2A and 2C, sPLA2s trigger, both on capacitated and uncapacitated sperm, the AR, from a very low dose such as 0.2 nM for mGX (FIG. 2B), in the absence of oocytes.

A sperm having realized AR is named acrosome-reacted sperm.

Acrosome-reacted sperm can thus not participate to the fertilization process since they are unable to cross the zone pellucida.

Capacitation is the process of sperm maturation (or activation); without capacitation, sperm is unable to fertilize the egg.

Thus, an advantage of the invention is to select sperms having had an efficient capacitation, or maturation, from sperms having had an inefficient or no capacitation at all.

Below 0.2 nM, sPLA2 does not trigger anymore the AR.

Above 200 nM, the AR is no more increased.

It must be noted that a 100 nM concentration of sPLA2 is equivalent to 1 mg/L of sPLA2.

Thus, another advantage of the invention is that sPLA2s are able to modulate key events of sperm physiology.

It must also be noted that as described in example 3, an endogenous mGX is also released during AR by sperm. Therefore, in the case where mGX is used to trigger the AR, and thus modulate the fertilization, the concentration above defined corresponds to endogenous mGX and exogenous mGX.

The endogenous mGX concentration being less than 0.1 nM, that means that at higher concentrations such as the ones above cited, the endogenous concentration is insignificant compared to the exogenous sPLA2 used.

The concentration 0.2 nM represents less than 50% endogenous sPLA2 and more than 50% of exogenous sPLA2.

In an advantageous embodiment, the sPLA2 used above at a concentration from 0.2 nM to less than 2 nM is constituted of endogenous sPLA2 and exogenous sPLA2.

In an advantageous embodiment, the sPLA2 used above at a concentration from 2 nM to 200 nM is constituted of exogenous sPLA2, the amount of endogenous sPLA2 being insignificant.

In an advantageous embodiment, the present invention relates to the use of sPLA2 above defined, wherein said fertilization, in particular the in vitro oocyte fertilization, is increased with a yield rate higher than 40%.

With sperm obtained from OF1 males, the rate of two cells embryos stage obtained at 24 hours is dose dependent and increases from 45% with control sperm to 65% with sperm treated with mGX at 200 nM.

Example 8 and FIG. 5A show the results obtained on IVF with an OF1 mouse strain (strain without fertility problems). With sperm obtained from C57B1/6 males (mouse strain known to have fertility problems), the rate of two-cells embryos stage obtained at 24 hours is dose dependent and increases from 8.2% with control sperm to 19.9% with sperm treated with mGX at 200 nM. Thus, in C57B1/6 strain, the fertilization rate, scored as the rate of 2-cells embryos obtained at 24H00, increases of 142% with mGX treated sperm in comparison to non-treated sperm.

Therefore, with the use of sPLA2 of the present invention, the maturation of sperm is not only modified but also the fertilization and the viable embryogenesis are also improved in two different strains.

In an advantageous embodiment, the invention relates to the use of secreted phospholipase and/or at least one metabolite produced by said $sPLA_2$ wherein said at least one metabolite is selected from the list consisting of fatty acids or lyso-phopholipids, in particular from arachidonic acid, myristoleic acid, palmitoleic acid, sapienic acid, oleic acid, linoleic acid, α-linolenic acid, eicosapentaenoic acid, docosahexaenoic acid, lysophosphatidylcholine, lysophosphatidylethanolamine, lysophosphatidylserine, lysophosphatidylinositol, lysophosphatidylglycerol, lysophosphatidate.

In an advantageous embodiment, the invention relates to the use of secreted phospholipase and/or at least one metabolite produced by said $sPLA_2$ wherein said metabolites are arachidonic acid and lysophosphatidylcholine.

In an advantageous embodiment, the invention relates to the use of at least one metabolite produced by said $sPLA_2$ wherein said metabolites are arachidonic acid and lysophosphatidylcholine.

In an advantageous embodiment, the invention relates to the use of secreted phospholipase and/or at least one metabolite produced by said $sPLA_2$, wherein said metabolite is at a concentration comprised from about 0.1 µM to about 50 µM, preferably from about 1 µM to about 50 µM, more preferably from about 1 µM to about 10 µM, in particular about 10 µM.

In an advantageous embodiment, the invention relates to the use of secreted phospholipase A2 (sPLA2) as defined above, liable to prevent said fertilization for the manufacture of a contraceptive drug.

By the expression "prevent the fertilization", it must be understood an absence of fertilization.

By "contraceptive drug" is meant a drug leading to an absence of fertilization.

In an advantageous embodiment, the sPLA2 above defined present the property to hydrolyse the sn-2 ester of one or more glycero-phospholipids with a specific activity higher than about 25 µmol/min/mg, in particular higher than about 50 µmol/min/mg on anionic and zwitterionic phospholipids.

Thus, in this embodiment, the specific activity of the sPLA2 must be the opposite to the one described for increasing the fertilization and thus sPLA2 used prevents the fertilization of Mammals.

Preferably, in the present invention, "the specific activity of sPLA2 higher than about 25 µmol/min/mg, in particular higher than about 50 µmol/min/mg" is towards one, two, three, four or five glycero-phospholipids, and more preferably towards one, two or three glycero-phospholipids.

In particular, "the specific activity of sPLA2 higher than about 25 µmol/min/mg, in particular higher than about 50 µmol/min/mg" is towards one glycero-phosphoslipid.

More particularly, "the specific activity of sPLA2 higher than about 25 µmol/min/mg, in particular higher than about 50 µmol/min/mg" is towards two glycero-phospholipids.

In this embodiment, the specific activity of sPLA2 can be higher than about 50 µmol/min/mg towards a first glycero-phospholipid and higher than about 25 µmol/min/mg towards a second glycero-phospholipid but it can also be about higher than about 25 µmol/min/mg towards both glycero-phospholipids or higher than about 50 µmol/min/mg towards both glycero-phospholipids.

In particular, "the specific activity of sPLA2 higher than about 25 µmol/min/mg, in particular higher than about 50 µmol/min/mg" is towards three glycero-phospholipids.

In this embodiment, the specific activity of sPLA2 can be:
  higher than about 50 µmol/min/mg towards three glycero-phospholipids or,
  higher than about 50 µmol/min/mg towards a first glycero-phospholipid and higher than about 25 µmol/min/mg towards two other glycero-phospholipids, or
  higher than about 50 µmol/min/mg towards two glycero-phospholipids and higher than about 25 µmol/min/mg towards a third glycero-phospholipids or,
  It can also be higher than about 25 µmol/min/mg towards three glycero-phospholipids.

It must be noted that in the case where the specific activity of one sPLA2 towards a glycero-phospholipid to obtain an increased fertilization is comprised from about 1 µmol/min/mg to about 25 µmol/min/mg, the needed specific activity of sPLA2 towards the same glycero-phospholipid to prevent the fertilization must be higher than about 25 µmol/min/mg.

In the case where the specific activity towards a glycero-phospholipid to obtain an increased fertilization is comprised from about 1 µmol/min/mg to about 50 µmol/min/mg, the needed specific activity towards the same glycero-phospholipid to prevent the fertilization must be higher than about 50 µmol/min/mg.

In an advantageous embodiment, glycero-phospholipids hydrolyzed by the sPLA2 above defined are selected from the list consisting of: 1-palmitoyl-2-oleoyl-sn-glycero-3-phosphoglycerol (POPG), 1-palmitoyl-2-oleoyl-sn-glycero-3-phosphocholine (POPC), 1-palmitoyl-2-oleoyl-sn-glycero-3-phosphoserine (POPS).

In an advantageous embodiment, the specific activity of sPLA2 towards POPC is higher than about 25 µmol/min/mg, in particular higher or equal to 30 µmol/min/mg.

The specific activity if sPLA2 towards POPC is the most important to prevent said fertilization compared to the one towards POPG and/or POPS. For instance, the toxic taipan recombinant sPLA2 OS2 (described as in "Lambeau G, Barhanin J, Schweitz H, Qar J, Lazdunski M. (1989) Identification and properties of very high affinity brain membrane-binding sites for a neurotoxic phospholipase from the taipan venom. J Biol Chem. 264:11503-10) having the following specific activity (determined as in Rouault et al 2006 Biochemistry 2006, 45, 5800): POPC: 59 µM/min/mg, POPG: 471 µM/min/mg and POPS: 23 µM/min/mg) decreases the number of viable 2-cell embryos while increasing the number of dead embryos as shown in FIG. 6.

In an advantageous embodiment, the specific activity of sPLA2 above defined towards POPC is higher than about 25 µmol/min/mg, in particular 30 µmol/min/mg, and/or the specific activity of sPLA2 towards POPG is higher than about 50 µmol/min/mg, in particular>250 µmol/min/mg, and/or the specific activity of sPLA2 towards POPS is higher than about 50 µmol/min/mg, in particular>250 µmol/min/mg.

In another preferred embodiment, sPLA2 above defined is used at a concentration from about 0.2 nM to about 200 nM, preferably from about 0.2 nM to about 20 nM, more preferably from 0.2 to 2 nM, more preferably from about 2 nM to about 200 nM, more preferably from about 2 nM to about 20 nM, more preferably from about 20 nM to about 200 nM, in particular about 200 nM.

In an advantageous embodiment, the sPLA2 used to prevent the fertilization is a sPLA2 of animal venom origin, in particular selected from arthropod or snake venoms, more particularly *Apis* spp, *Oxyuranus* spp and *Daboia* spp., or an homologous protein thereof produced as a recombinant protein.

In another aspect, the present invention relates to a pharmaceutical composition comprising sPLA2 defined above as an active substance, in association with a pharmaceutically acceptable vehicle.

In this embodiment, the pharmaceutical composition is able to increase or decrease (or prevent) the fertilization depending on the dosage of sPLA2.

The pharmaceutical composition can be under various galenic forms, in particular solid form such as powder, or semi solid form, such as cream or gel, or liquid form, such as lotion or solution.

The pharmaceutical composition can be administered, in vitro, under powder form or solution form to the medium wherein the fertilization, the capacitation or the sorting of spermatozoa is carried out, to increase the fertilization or under vaginal jelly (gel), films, sponge or foam forms to decrease the fertilization.

For promoting fertilization use, the sPLA2 liable to increase said fertilization (for instance mGX), could be used from about 0.2 µg/ml to about 20 µg/ml, preferably from about 0.2 µg/ml to about 10 µg/ml, more preferably from about 1 µg/ml to about 5 µg/ml, in particular 2 µg/ml, of sperm incubating medium.

For contraceptive use, sPLA2 liable to decrease said fertilization (for instance OS2), could be used from about 0.5 µg/ml to about 50 µg/ml, preferably from about 0.5 µg/ml to about 20 µg/ml, more preferably from about 1 µg/ml to about 10 µg/ml, in particular 5 µg/ml, of vaginal gel or foam.

In an advantageous embodiment, the present invention relates to the use of the pharmaceutical composition defined above, wherein said sPLA2 is a purified protein of a Mammalian origin, in particular selected from Groups IIA IIF, III, V or X sPLA2, more particularly mouse GX or human GV or human GX, or of prokaryotic origin such as bacterial origin, plant origin, or of other origins including for instance animal venoms, in particular selected from arthropod or snake venoms, more particularly *Apis* spp, *Oxyuranus* spp and *Daboia* spp., or an homologous protein thereof produced as a recombinant protein.

In another aspect, the present invention relates to sPLA2 as defined above, for the treatment of sterility or for promoting or improving the fertilization or for promoting or improving the viable embryogenesis of a Mammal, in particular a female Mammal undergoing in vitro fertilization (IVF), gamete intrafallopian transfer procedure (GIFT), intracytoplasmic sperm injection (ICSI), or therapeutic donor insemination (TDI) during assisted reproductive technologies (ART).

In still another aspect, the present invention relates to sPLA2 as defined above, for the contraception of Mammals.

In another aspect, the present invention relates to a process of in vitro selection of spermatozoa comprising the following steps:
a. treating sperm at the concentration of 1 million cells/ml, previously collected, with 0.5-2% bovine serum albumen (BSA) or any compounds binding cholesterol to obtain capacitated sperm,
b. incubating capacitated sperm at the concentration of 1 million cells/ml with sPLA2 having a specific activity as defined above, at a concentration from about 0.2 nM to about 200 nM, preferably from about 0.2 nM to about 20 nM, more preferably from 0.2 to 2 nM, more preferably from about 2 nM to about 200 nM, more preferably from about 2 nM, to about 20 nM more preferably from about 20 nM to about 200 nM, in particular about 200 nM, and/or metabolites of sPLA, as defined above, at a concentration comprised from about from about 0.1 µM to about 50 µM, preferably from about 1 µM to about 50 µM, more preferably from about 1 µM to about 10 µM, in particular about 10 µM, to obtain a mixture of acrosome-reacted sperm and non-acrosome-reacted sperm,
c. isolating non-acrosome-reacted sperm after washing and centrifugating and discarding acrosome-reacted sperm.

Step a. is necessary to capacitate sperm.

The incubation in step b. must be carried out with a sPLA2 having a specific activity comprised from about 1 to about 50 µmol/min/mg, in particular about 1 µmol/min/mg to about 25 µmol/min/mg towards one or more glycerol-phospholipids.

The incubation time of capacitated sperm with sPLA2 can be comprised from about 0.1 minute to about 2 hour, preferably from about 1 minute to about 1 hour, preferably from about 1 minute to about 30 minutes, more preferably from about 5 to about 15 minutes, in particular about 10 minutes. The 10 minute time corresponds to the kinetic parameter allowing obtaining the maximum acrosome reaction.

Above 2 hours, the DNA will be fragmented and therefore deficient.

Below 0.1 minute, the incubation time is too low to trigger an acrosome reaction.

The incubation time of capacitated sperm with metabolites of sPLA can be comprised from about 0.1 minute to about 2 hours, preferably from about 1 minute to about 1 hour, preferably from about 15 minutes to about 1 hour, more preferably from about 30 to about 45 minutes, in particular about 45 minutes.

The 45 minute time corresponds to the kinetic parameter allowing obtaining the maximum acrosome reaction.

The incubation time capacitated sperm with sPLA2 and metabolites of sPLA can be comprised from about 0.1 minute to about 2 hours, preferably from about 1 minute to about 1 hour, preferably from about 15 minutes to about 1 hour, more preferably from about 30 to about 45 minutes, in particular about 45 minutes.

sPLA2 metabolites can be also introduced when sperm and oocytes are mixed, and corresponding to the fertilization process (FIG. 7). sPLA2 metabolites are present in the fertilization medium until the first sperm wash (4 hours).

In the beginning of step b., i.e. after capacitation of sperm and before incubating with sPLA2 and/or metabolites of sPLA, the capacitated sperm comprise a mixture of sperm of efficient quality and sperm of deficient quality, having in particular a fragmented DNA and a modification of lipids composition of the plasma membrane.

It has been observed that when the sperm DNA quality is low, there is an increase of the phospholipids in the sperm membrane and in particular of POPS that will be therefore eliminated by the incubation step leading thus to an increase sperm quality.

The step c. eliminates deficient acrosome-reacted sperm and leads to the obtaining of concentrated sperm with a high quality.

Another advantage of the invention is that the incubation of said mixture with sPLA2 causes the hydrolysis of deficient spermatozoa leading to a selection of efficient spermatozoa, which could be used further, in particular in ART, to improve the fertilization rate, the viable embryos rate and thus a decreased risk of birth defects.

In another aspect, the present invention relates to a process of in vitro fertilization comprising the following steps:
  a. treating sperm at the concentration of 1 million cells/ml, previously collected, with 0.5-2% bovine serum albumen (BSA) or any compounds binding cholesterol to obtain capacitated sperm,
  b. incubating capacitated sperm at the concentration of 1 million cells/ml with sPLA2 having a specific activity as defined above, at a concentration from about 0.2 nM to about 200 nM, preferably from about 0.2 nM to about 20 nM, more preferably from 0.2 to 2 nM, more preferably from about 2 nM to about 200 nM, more preferably from about 2 nM to about 20 nM more preferably from about 20 nM to about 200 nM, in particular about 200 nM, and/or metabolites of sPLA, as defined above, at a concentration comprised from about 0.1 µM to about 50 µM, preferably from about 1 µM to about 50 µM, more preferably from about 1 µM to about 10 µM, in particular about 10 µM, to obtain a mixture of acrosome-reacted sperm and non-acrosome-reacted sperm,
  c. contacting said non-acrosome-reacted sperm at a concentration of 50000/ml, after washing and centrifugating, with 20 to 100 oocytes previously collected.

Steps a and b are similar to the above defined process leading to improve matured sperm.

Step c. consists in contacting the matured and non-acrosome-reacted sperm with oocytes to carry out the fertilization with a better rate and an improved embryogenesis.

Thus, the present invention can treat male infertility.

Indeed, in case of male infertility, the treatment of sperm leads to a selection of efficient spermatozoa and therefore, it is possible to have a treated sperm enriched with matured spermatozoa that can either be introduced in a female human organism in order to carry out the fertilization and embryogenesis or contacted with oocytes previously collected in order to carry out the in vitro fertilization and embryogenesis and thus obtain viable and healthy embryos.

In an advantageous embodiment, the process above defined increases the fertilization rate.

The incubation of capacitated sperm with sPLA2 and/or metabolites of sPLA allows discarding the major part of deficient spermatozoa and thus improves the fertilization rate and thus increases the number of viable and healthy embryos obtained after the fertilization step.

In another aspect, the present invention relates to a process of predicting fertility in a Mammal comprising the following steps:
  a. treating sperm at the concentration of 1 million cells/ml, previously collected, with 0.5-2% bovine serum albumen (BSA) or any compounds binding cholesterol to obtain capacitated sperm.
  b. incubating capacitated sperm at the concentration of 1 million cells/ml with sPLA2 having a specific activity as defined above, at a concentration from about 0.2 nM to about 200 nM, preferably from about 0.2 nM to about 20 nM, more preferably from 0.2 to 2 nM, more preferably from about 2 nM to about 200 nM, more preferably from about 2 nM to about 20 nM more preferably from about 20 nM to about 200 nM, in particular about 200 nM, and/or metabolites of sPLA, as defined above, at a concentration comprised from about from about 0.1 µM to about 50 µM, preferably from about 1 µM to about 50 µM, more preferably from about 1 µM to about 10 µM, in particular about 10 µM, to obtain a mixture of acrosome-reacted sperm and non-acrosome-reacted sperm,
  c. determining the amount of acrosome-reacted sperm and comparing it relative to the amount of acrosome-reacted sperm obtained with a control Mammal,
  d. predicting that the Mammal is infertile if the amount of acrosome-reacted sperm determined in step c. is higher than the amount obtained with said control Mammal.

Steps a and b are similar to the above defined process.

As already discussed, the capacitated sperm comprise a mixture of sperm of efficient quality, and sperm of deficient quality, having in particular a fragmented DNA and a modification of lipids composition of the plasma membrane.

Therefore, in case where a Mammal is infertile the level of deficient sperm is higher compared to the control, and thus treating sperm with sPLA2 and/or metabolites of sPLA liable to increase said fertilization, leads to a higher amount of acrosome-reacted sperm compared to the control.

In another aspect, the present invention relates to a process of contraception comprising a step of contacting Mammal sperm with sPLA2 having a specific activity as defined above.

The specific activity is the same as defined above for the fertilization.

The contraception can be carried out, for instance, by vaginal application of a gel, a film, a foam or a sponge containing sPLA2.

Figure 1:
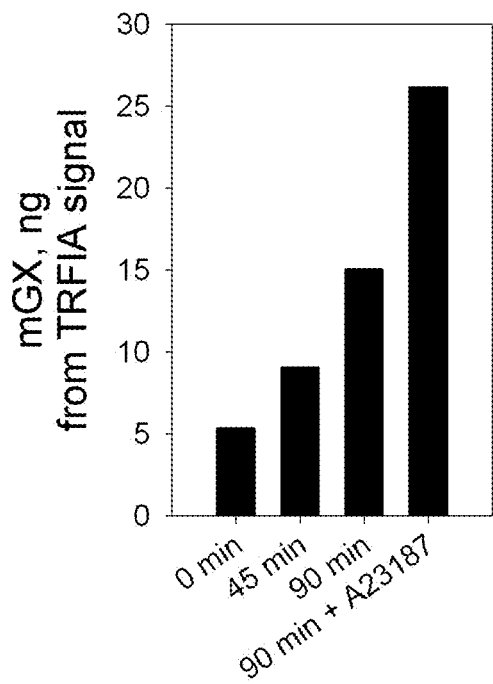
FIG. 1 shows that mGX is released during acrosome reaction and thus is localized in the acrosome of the sperm
  A. mGX is measured with time-resolved fluorescence immunoassay (TRFIA) in the capacitation medium containing 2% bovine serum albumin (BSA) at different times of capacitation: 0, 45 and 90 minutes and at 90 minutes in the presence of the calcium ionophore A23187 during the last 30 minutes of capacitation. The A23187 produces a two fold increase of mGX level in the capacitation medium.
  The x-axis corresponds to time of capacitation (0, 45 and 90 minutes and 90 minutes in presence of A23187 from left to right columns)
  The y-axis corresponds to the mGX concentration (ng)
  B. sPLA2 activities are measured using radiolabeled E. coli membranes as substrate. Sperm were subjected to centrifugation after a variable duration of capacitation and sPLA2 activities were measured in the sperm pellet and in the supernatant at 0, 45 and 90 minutes and at 90 minutes in the presence of the calcium ionophore A23187 during the last 30 minutes of capacitation.
  The x-axis represents the time of capacitation:
  0, 45, 90 minutes, 90 minutes plus A23187 during the last 30 minutes, for the four first black columns of supernatant
  0, 45, 90 minutes, 90 minutes plus A23187 during the last 30 minutes, for the four last black columns of the pellet;
  The y-axis represents the total activity in DPM.
Figure 1:
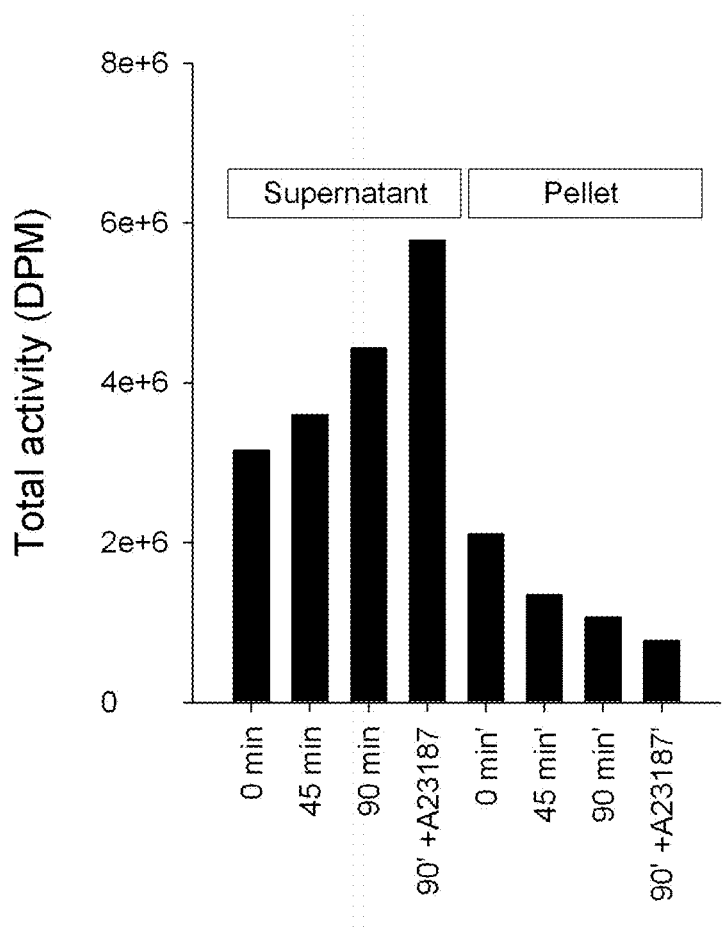

The x-axis represents the control, mGIIA, mGV, mGX from left to right columns.

The y-axis represents the percentage of acrosome-reacted (AR) sperm.

B. Dose-response curves of sPLA2-activated acrosome reaction. mGIIA (•) and mGX (○) sPLA2. The data are expressed as the percentage of sPLA2-induced acrosome reaction (obtained after subtracting spontaneous AR to total AR) in function of sPLA2 concentration, ranging from 0.2 nM to 500 nM. mGX is a highly potent activator of AR since low doses as 0.2 nM induce 15% of AR.

The x-axis represents the sPLA2 concentration (nM).

The y-axis represents the percentage of acrosome-reacted (AR) obtained above spontaneous AR.

C. mGX is able to trigger acrosome reaction of non-capacitated sperm (10 min) and of capacitated sperm (55 and 90 min) Spermatozoa were incubated with 2% BSA in a 5% $CO_2$ chamber at 37° C. Acrosome reaction triggered by sPLA2 has been compared to spontaneous acrosome reaction at 10, 55 and 90 min of capacitation.

The x-axis represents from left to right:

First column: non-capacitated sperm incubated 10 min without mGX.

Second column: non-capacitated sperm incubated 10 min with mGX.

Third column: capacitated sperm incubated 55 min without mGX.

Fourth column: capacitated sperm incubated 55 min with mGX.

Fifth column: capacitated sperm incubated 90 min without mGX.

Sixth column: capacitated sperm incubated 90 min with mGX.

The y-axis represents the percentage of acrosome-reacted (AR) sperm.

Figure 3:
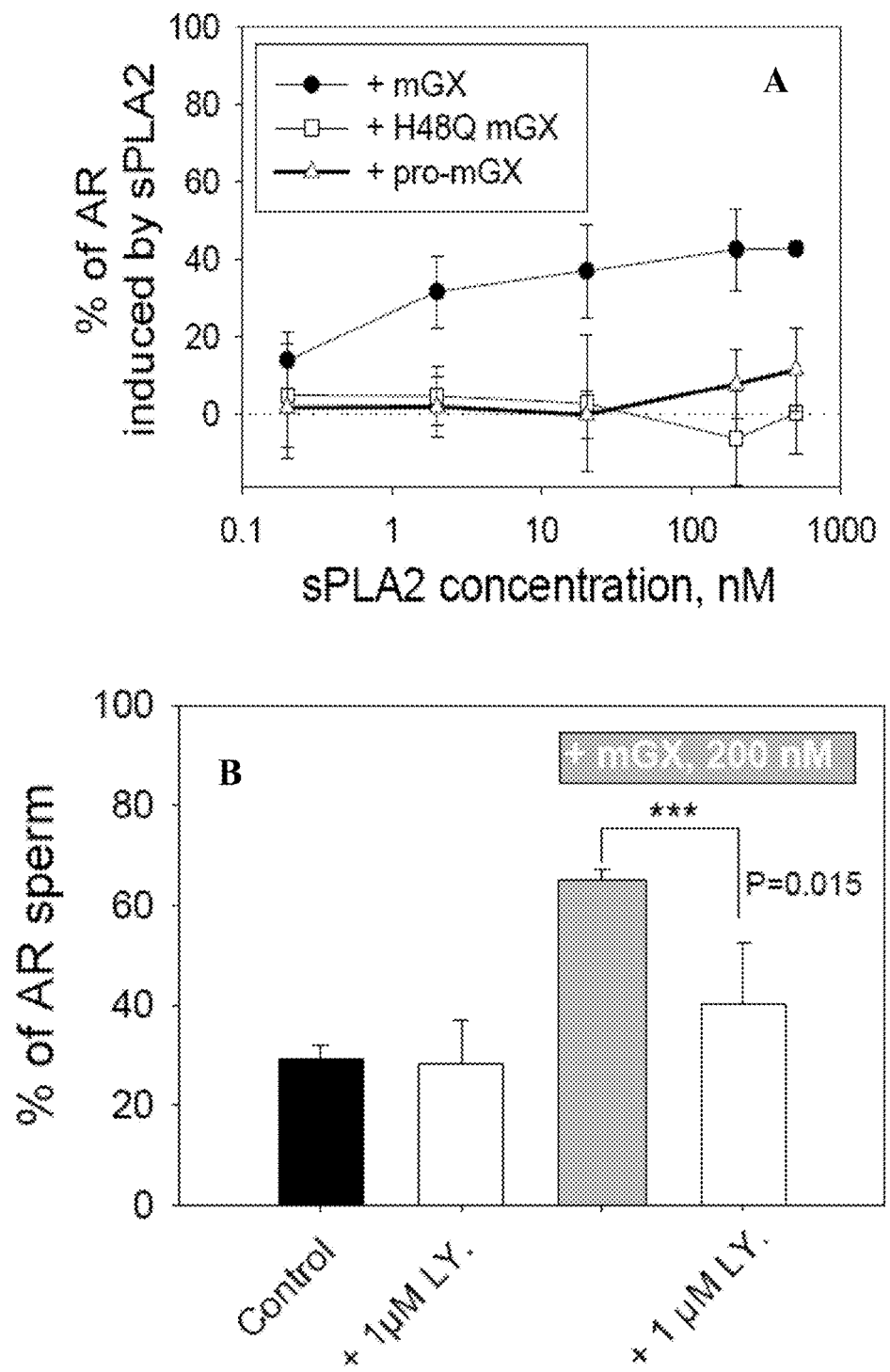
Figure 3:
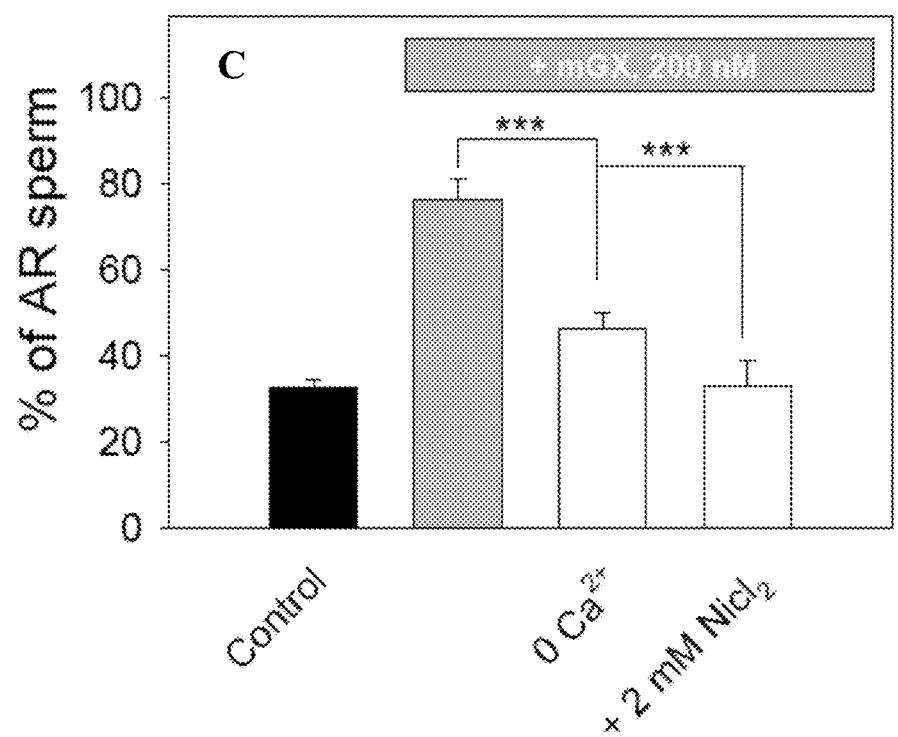

FIG. 3 shows that the enzymatic activity of mGX is required to trigger acrosome reaction.

A. Mutation of the catalytic site of mGX (H48Q) abolishes its ability to trigger sperm acrosome reaction (□). Pro-mGX, the inactive pro-enzyme of mGX is also unable to trigger sperm acrosome reaction (Δ) in comparison to control mGX (•).

The x-axis represents the sPLA2 concentration (nM).

The y-axis represents the % of AR induced by sPLA2.

B. The specific sPLA2 inhibitor LY329722 blocks the ability of mGX to trigger acrosome reaction. The rate of AR of capacitated sperm incubated transiently 10 min with the mGX inhibitor LY329722 (left white bar) is similar to those of non-treated sperm (black bar), showing that LY329722 by itself does not modify AR. On the other hand, 1 µM Ly329722 blocks AR induced by 200 nM mGX (right white bar versus grey bars).

The x-axis represents from left to right columns:
Black bar: non-treated sperm.
White bar: sperm+LY329722.
Grey bar: sperm+mGX (200 nM).
White bar: sperm+mGX (200 nM)+LY329722.
The y-axis represents the % of acrosome-reacted sperm.

C. Removing external calcium (n=3) or adding 2 mM $Ni^{2+}$ (n=3) in the bath block the ability of mGX to trigger acrosome reaction.

The x-axis represents from left to right column:
Black bar: non-treated sperm.
Grey bar: sperm+mGX (200 nM)
Left white bar: sperm+mGX (200 nM) without $Ca^{++}$
Right white bar: sperm+mGX (200 nM) with 2mM $Ni^{2+}$.
The y-axis represents the % of acrosome-reacted sperm.

Figure 4:
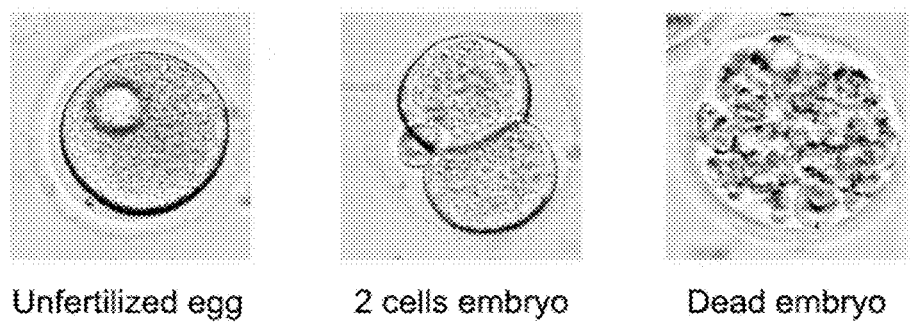

FIG. 4 shows the photographs of the different stages reached by oocytes at 24 h00 after fertilization (from left to right):

"Unfertilized egg" (UF) corresponds to oocytes with one polar body

"Two-cell embryos" corresponds to normal development of embryo

"Dead embryos" corresponds either to oocytes presenting both polar bodies but no cell division or multiple and uncontrolled divisions.

Figure 5:
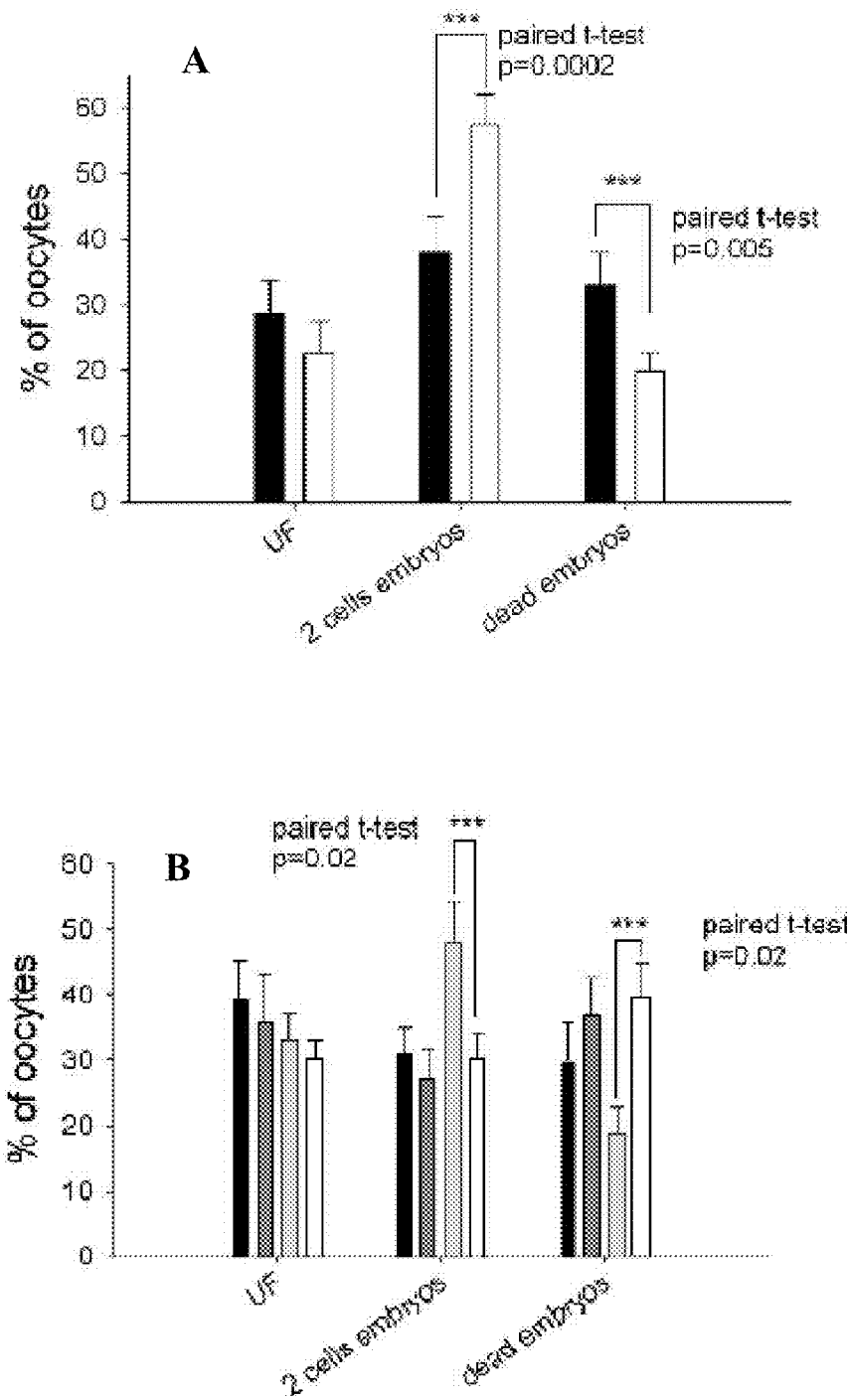

FIG. 5 shows that exogenous mGX promotes fertilization with sperm allowing a better embryo development.

A. Yield of IVF realized with sperm from OF1 males (black bars, n=13), and sperm treated with 200 nM mGX (white bars, n=13). Before to be mixed with oocytes, sperm were capacitated 35 min in M16-2% BSA. At 35 min, sperm cells were incubated for 10 min with either control medium or 200 nM mGX, in M16 culture medium. For each experiment (n=13 different males), the number of oocytes used was between 20 and 58 oocytes.

The x-axis represents from left to right set of bars:
First set:
Unfertilized (UF): sperm (black bar), sperm treated with mGX (200 nM) (white bar).
Second set:
2 cells embryos: sperm (black bar), sperm treated with mGX (200 nM) (white bar).
Third set:
Dead embryos: sperm (black bar), sperm treated with mGX (200 nM) (white bar).
The y-axis represents the % of oocytes reaching the corresponding stages.

B. The exogenous effect of mGX is blocked by the sPLA2 inhibitor LY329722. Yield of IVF obtained with sperm from OF1 males (black bars, n=6), sperm treated with 1 µM of the sPLA2 inhibitor LY329722 (dark grey bars), sperm treated with 200 nM mGX (light grey bars) and sperm treated with 200 nM mGX preincubated with 1 µM LY329722 (white bars). For each experiment (n=6 different males), the number of oocytes used was between 20 and 58 oocytes.

The x-axis represents from left to right set of bars:
First set:
Unfertilized (UF): sperm (black bar), sperm treated with LY329722 (1 µM) (dark grey bar), sperm treated with mGX (200 nM) (light grey bar), and sperm treated with a mixture of LY329722 (1 µM) and mGX (200 nM).
Second set:
2 cells embryos: sperm (black bar), sperm treated with LY329722 (1 µM) (dark grey bar), sperm treated with mGX (200 nM) (light grey bar), and sperm treated with a mixture of LY329722 (104) and mGX (200 nM).
Third set:
Dead embryos: sperm (black bar), sperm treated with LY329722 (1 µM) (dark grey bar), sperm treated with mGX (200 nM) (light grey bar), and sperm treated with a mixture of LY329722 (1 µM) and mGX (200 nM).
The y-axis represents the % of oocytes reaching the corresponding stages.

Before being mixed with oocytes, spermatozoa were capacitated 35 min in M16-2% BSA. At 35 min, sperm cells were incubated for 10 min with either control medium or 200 nM mGX, in M16 culture medium. After treatment, drugs are removed by centrifugation and wash in order to remove unbound drug and lipid metabolites produced during the sPLA2 incubation. Control sperm underwent the same washing protocol at 35 min of capacitation. After drug washing, the concentration of remaining drug was estimated at 1 nM. To check that this concentration of sPLA2 did not induce artefact effects on sperm-oocyte fusion (Riffo, M. S. and M. Parraga. 1997. Role of phospholipase A2 in Mammalian sperm-egg fusion: development of hamster oolemma fusibility by lysophosphatidylcholine. J. Exp. Zool. 279:81-88), we realized control IVF experiments where sperm and oocytes were incubated with 1 nM mGX: no difference was noticed (data not shown).

Figure 6:
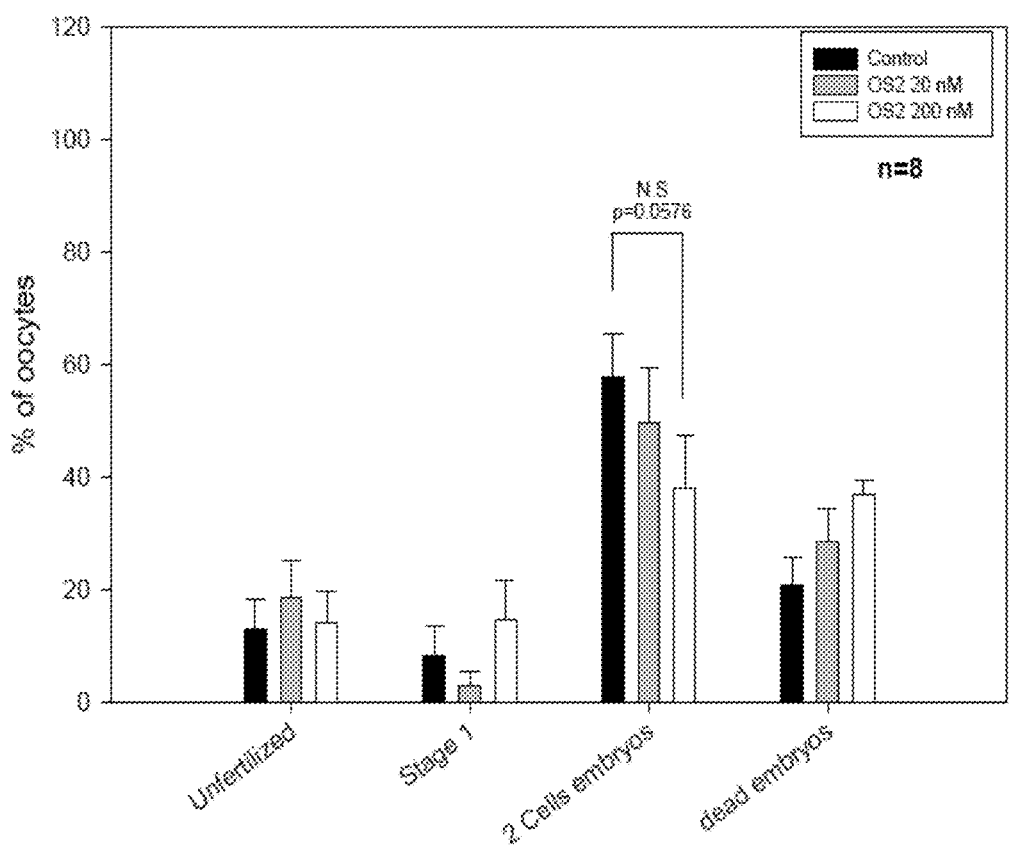

FIG. 6 shows that the taipan toxic sPLA2 OS2 inhibits IVF.
Yield of IVF realized with sperm from OF1 males (black bars), sperm treated with 20 nM OS2 (grey bars) and sperm treated with 200 nM OS2 (white bars). For each experiment (n=8 different males), the number of oocytes used was between 20 and 60 oocytes.
The x-axis represents from left to right set of bars:
First set:
Unfertilized (UF): sperm (black bar), sperm treated with OS2 (20 nM) (grey bar), sperm treated with OS2 (200 nM) (white bar).
Second set:
Stage 1 (one cell or fertilized cell): sperm (black bar), sperm treated with OS2 (20 nM) (grey bar),
sperm treated with OS2 (200 nM) (white bar).
Third set:
2 cells embryos: sperm (black bar), sperm treated with OS2 (20 nM) (grey bar), sperm treated with OS2 (200 nM) (white bar).
Fourth set:
Dead embryos: sperm (black bar), sperm treated with OS2 (20 nM) (grey bar), sperm treated with OS2 (200 nM) (white bar). The y-axis represents the % of oocytes reaching the corresponding stages.

Figure 7:
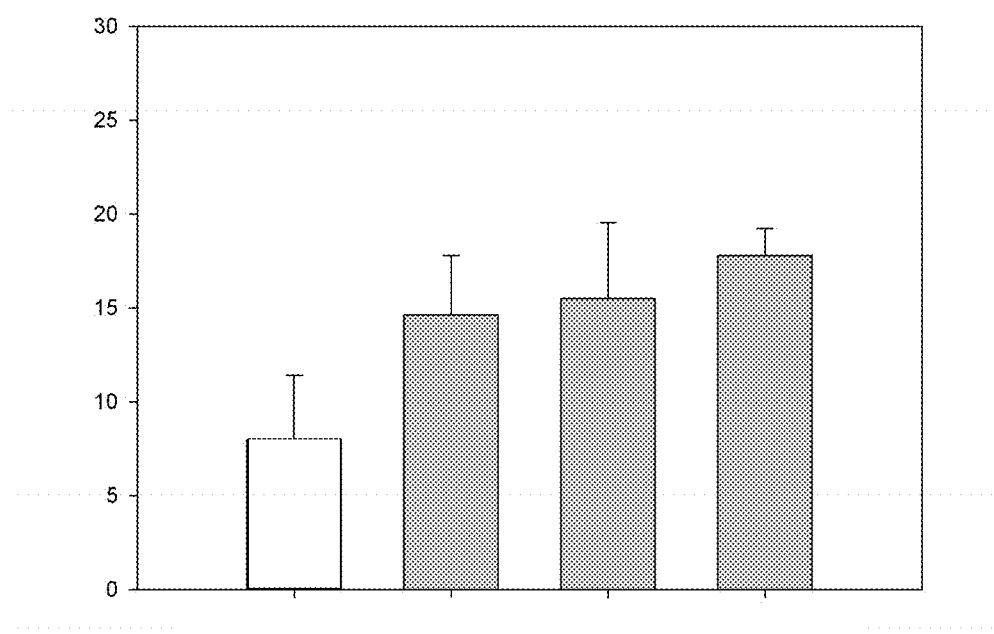
Figure 8:
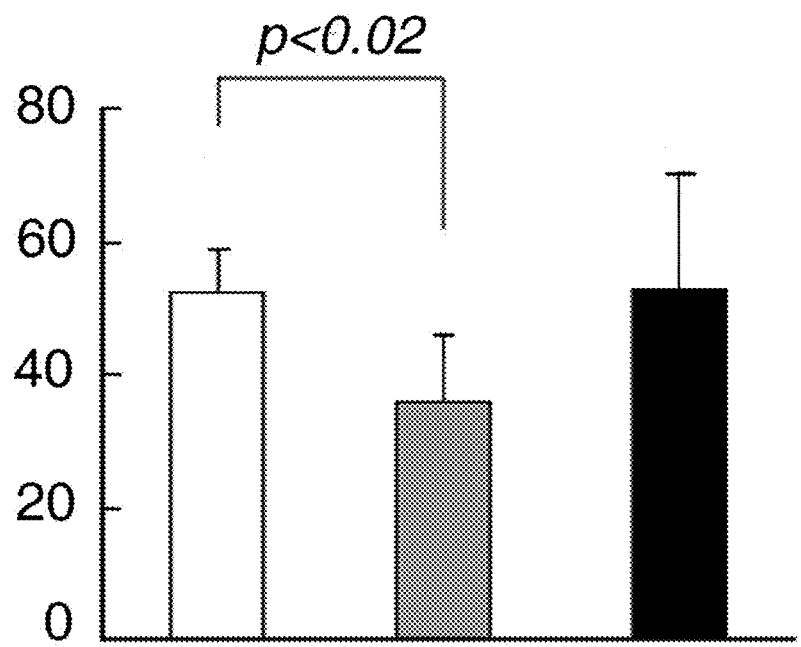

FIG. 7 shows the improvement of fertilization by using sPLA2 (mGX) or both arachidonic acid and lysophosphocholine.
sPLA2 at 200 nM, or its metabolites at a concentration of 10 µM, improve fertilization outcome. Acid arachidonic (AA) and Lysophocholine (LPC, from eggs) were introduced either during the capacitation process during 45 min or after gamete mixing, during the fertilization process during 4 h.
X-axis: from left to right: control, mGX (200 nM), LPC-AA (10 µM) during capacitation, LPC-AA during fertilization.
Y-axis: percentage of 2 cell embryo at 24 h post fertilization FIG. 8 shows the rescue of the fertilization with lysophosphocholine LPC at 1 µM after blocking endogenous mGX sPLA2 with LY329722.
Blocking endogenous mGX sPLA2 released during spontaneous acrosome reaction occurring during capacitation by a specific sPLA2 inhibitor (LY329722) decreased fertilization outcome. This decrease was rescued by adding during the capacitation process LPC at a concentration of 1 µM.
X-axis: from left to right: control, LY329722 (2 µM), LY329722 (2 µM)+LPC (1 µM) during capacitation.
Y-axis: percentage of 2 cell embryo at 24 h post fertilization

EXAMPLES

Example 1

Acrosome Reaction Assay

Sperm cells from caudae epididymes were allowed to swim in M2 medium for 10 min. Then, sperms were incubated, if necessary, with different sPLA2 in M16 medium at 37° C. for 10 min. Cells were transferred in PBS solution and then fixed with 4% PFA solution for 2 min. Sperm was washed with 100 mM ammonium acetate for 2 min and wet-mounted on slides and allowed to air dry. Slides were then rinsed with water and stained with coomassie blue (0.22%) for 2 min and finally rinsed with water. Slides were counted immediately and 150 sperm cells were scored at least.

Example 2

Electron Microscopy

Sperm cells were fixed with 2.5% glutaraldehyde in 0.1 M cacodylate buffer pH 7.4 during 2 hours at room temperature. Cells were then washed with buffer and post fixed with 1% Osmium tetroxyde in the same buffer during 1 hour at 4° C. After extensive washing with water cells were then stained with 0.5% uranile acetate pH 4 overnight at 4° C. Cells were then dehydrated through graded alcohol (30%-60%-90%-100%-100%-100%) and infiltrate with a mix of 1/1 epon/alcohol 100% during 1 hour before several bath of fresh epon (Flukka) during 3 hours. Finally, cells were centrifugated and immersed in fresh Epon and polymerised during 3 days at 60° C. Ultrathin sections of the cell pellet were cut with an ultra-microtome (Leica). Sections were post-stained with 4% uranile acetate and 1% lead citrate before being observed in an electron microscope at 80 kV (JEOL 1200EX).

Results: sPLA2 induced a morphologically normal acrosome reaction

It was important to check with electron microscopy (EM) that sPLA2 induced a morphologically normal acrosome reaction. The morphological criteria by which an acrosome reaction is evaluated to be normal are relatively limited: first, the outer acrosomal membrane should present vesiculation, second, the plasma membrane should fuse with the outer acrosomal membrane and present a characteristic double hair pin shape at the base of the acrosome (Green, D. P. (1978) The induction of the acrosome reaction in guinea-pig sperm by the divalent metal cation ionophore A23187. J. Cell Sci., 32:137-51.:137-151.)

For these experiments, uncapacitated sperm was used in order to reduce the contribution of spontaneous AR and 200 nM sPLA2 to get maximum sPLA2-induced AR. Sperm were incubated 10 min with mGX sPLA2 or the calcium ionophore A23187 and then fixed. In the presence of A23187, all acrosome-reacted sperm presented complete AR, with the 3 morphological criteria, as described above.

In the presence of sPLA2, very early stages of AR like cavitation of the acrosomal matrix were observed.

Sperm with complete sPLA2-induced AR were also evaluated as normal on the base of morphological criteria.

This result suggests that sPLA2-induced AR presents normal morphological feature but with a kinetic slower than those observed with the calcium ionophore A23187.

Example 3

Detection of mGX sPLA2 in Sperm Cells

Sperm cells from 4 caudae epididymes of mGX sPLA2 mice were allowed to swim for 15 min at 37° C. in 2.5 ml of M2 medium. Aliquots of 500 µl of sperm cells were then diluted in 4.5 ml of M16 medium containing 2% fatty acid free BSA and further incubated at 37° C. for 0, 45 and 90 min. In some assays, A23187 Ca2+ ionophore (5 µM) was added after the first 60 min of incubation and sperm cells were incubated for an additional 30 min. After incubation, sperm cells were spun down for 8 min at 1,200 rpm, and supernatants and cell pellets were flash frozen in liquid nitrogen and stored at −80° C. mGX sPLA2 protein expression and enzymatic activity were analyzed on crude cell supernatants and cell pellets after resuspension in 500 µl of M16 medium containing a cocktail of protease inhibitors (Complete inhibitor set, Roche Biochemicals) and lysis with a Branson 350 Sonifier Cell disrupter. Time-resolved fluoro-immunoassays (TR-FIA) for mGX sPLA2 was performed as described with minor modifications (Eerola, L. I., Surrel, F., Nevalainen, T. J., Gelb, M. H., Lambeau, G., and Laine, V. J. (2006) Analysis of expression of secreted phospholipases A2 in mouse tissues at protein and mRNA levels. Biochim. Biophys. Acta., 1761: 745-756). Briefly, 1 to 5 µl of protein sample were diluted in 100 µl of Delfia assay buffer (Tris-HCl buffered NaCl solution, pH 7.8, containing NaN3, BSA, bovine gamma globulins, Tween 40, DTPA and inert red dye, Perkin Elmer Wallac, Turku, Finland) and added to mGX sPLA2 IgG-coated microtiter wells previously washed twice with TR-FIA washing solution (10 mM Tris-HCl, pH 7.8, containing 0.9% NaCl, 0.04% NaN3 and 0.02% Tween 20). After incubation at room temperature with constant shaking at 200 cycles/min for 30 min, wells were washed four times with TR-FIA washing solution, incubated with 100 µl of Eu-labeled mGX IgG tracer (0.5 µg/ml diluted in Delfia Assay Buffer), and washed again four times as above. After washing, 100 µl of Delfia enhancement solution were added to wells, incubated at room temperature for 5 min with shaking at 200 cycles/min and thereafter for 10 min without shaking. Time-resolved fluorescence was measured using a Wallac Envision Perkin Elmer plate reader and optimized optical modules for DELFIA assays. sPLA2 enzymatic activity was measured using radiolabeled *E. coli* membranes as substrate (Rouault, M., Le Calvez, C., Boilard, E., Surrel, F., Singer, A., Ghomashchi, F., Bezzine, S., Scarzello, S., Bollinger, J., Gelb, M. H., and Lambeau, G. (2007) Recombinant production and properties of binding of the full set of mouse secreted phospholipases A2 to the mouse M-type receptor. Biochemistry., 46:1647-1662). Briefly, 5 to 50 µl of cell lysates or supernatants were incubated for 60 min in 300 µl of sPLA2 activity buffer (0.1 M Tris pH 8.0, 10 mM $CaCl_2$, and 0.1% bovine serum albumin containing 100,000 DPM of [3H]oleate-radiolabeled *E. coli* membranes. Reactions were stopped by addition of 300 µl of stop buffer (0.1 M EDTA pH 8.0 and 0.1% fatty acid free bovine serum Albumin); mixtures were centrifuged at 10,000 g for 5 min, and the supernatants containing released [$^3$H] oleate were counted.

Results:

The time-resolved fluorescence immunoassay (TRFIA) was used to investigate the presence of this enzyme in mature sperm cells. This technique is highly sensitive and allows eliminating the non-specific endogenous fluorescence. We dosed the presence of mGX in uncapacitated and capacitated sperm and in the supernatant medium. FIG. 1A shows that the specific mGX fluorescence increased in the supernatant medium during capacitation. In the presence of the calcium ionophore A23187, a strong inducer of AR, the level of specific florescence doubled. In the meanwhile, the activity decreased in the sperm cells. We measured also total sPLA2 enzymatic activity in sperm cells and in the surrounding incubated medium (supernatant) during capacitation (FIG. 1B). We found that sPLA2 enzymatic activity increased in the supernatant, in a similar manner of mGX specific fluorescence measured by TRFIA. These results showed that mGX was an active constituent of cellular machinery and was released during acrosome reaction in the supernatant medium.

Example 4

Production of Recombinant sPLA2s

Recombinant mouse sPLA2s group IIA, IID, IIE, V and X and the H48Q mutant mGX sPLA2 were produced as described previously (Rouault, M., Le Calvez, C., Boilard, E., Surrel, F., Singer, A., Ghomashchi, F., Bezzine, S., Scarzello, S., Bollinger, J., Gelb, M. H., and Lambeau, G. (2007) Recombinant production and properties of binding of the full set of mouse secreted phospholipases A2 to the mouse M-type receptor. Biochemistry., 46:1647-1662). Pro-mGX sPLA2 was produced as for mature mGX sPLA2 using the pAB3 vector in which the full-length cDNA coding for Pro-mGX was inserted in frame with the ΔGST protein and the factor Xa cleavage site, which were removed from Pro-mGX sPLA2 by using the factor Xa protease (Rouault, M., Le Calvez, C., Boilard, E., Surrel, F., Singer, A., Ghomashchi, F., Bezzine, S., Scarzello, S., Bollinger, J., Gelb, M. H., and Lambeau, G. (2007) Recombinant production and properties of binding of the full set of mouse secreted phospholipases A2 to the mouse M-type receptor. Biochemistry., 46:1647-1662).

Example 5

Effect of sPLA2 on Acrosome reaction

The effect of sPLA2 on acrosome reaction (AR) has been evaluated. This point was peculiarly important since the role of an endogenous PLA2 during AR has been raised from several arguments (see introduction and reviewed by Roldan, E. R. and Q. X. Shi. 2007. Sperm phospholipases and acrosomal exocytosis. Front Biosci. 12:89-104.:89-104). However, the ability of the different Mammalian sPLA2 to trigger AR when added in the culture medium was not tested so far.

Figure 2:
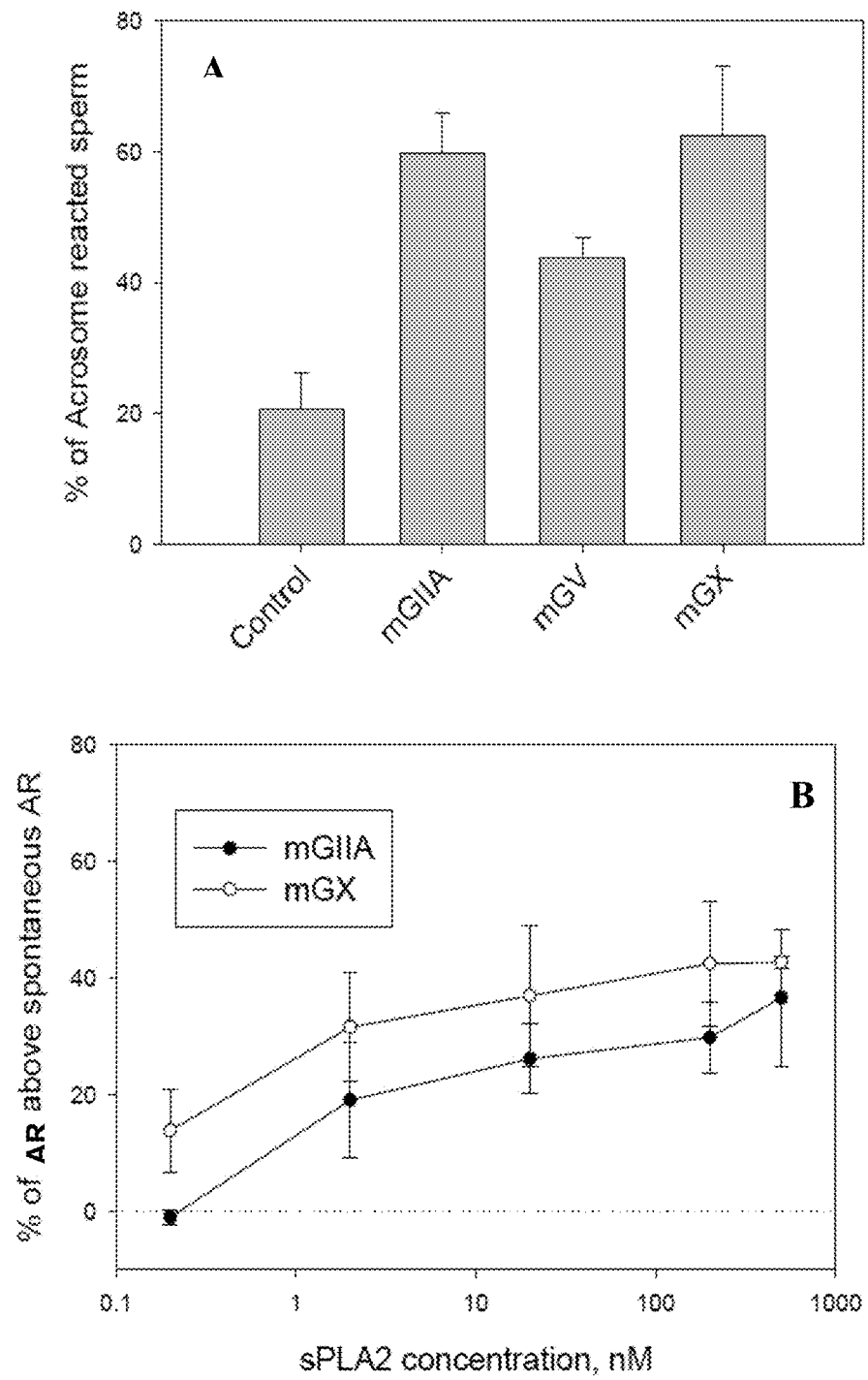
FIG. 2 shows that sPLA2s are potent activators of acrosome reaction A. Three different sPLA2 belonging to 3 different groups (group IIA, group V and group X) trigger acrosome reaction. Sperm were incubated 10 min with 200 nM of sPLA2 and subsequently fixed and stained with coomassie blue. At least 200 sperm were counted per slide.
Figure 2:
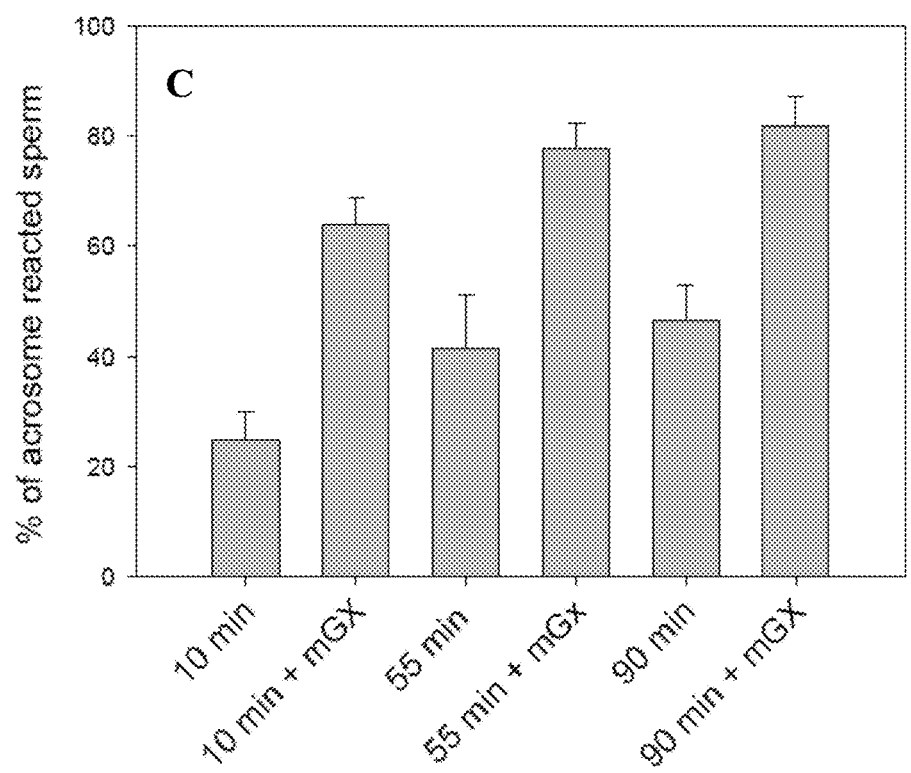

Several sPLA2 known to be present in the biological fluids surrounding sperm cells have been tested.

a) sPLA2 is able to trigger AR on uncapacitated sperm.

mGIIA and mGX and in a lesser extent mGV, were able to trigger AR on uncapacitated sperm. (FIG. 2A).

The rate of AR increase from 20%, corresponding to spontaneous acrosome-reacted sperm, to 60% in the presence of 200 nM active sPLA2. In order to better characterize the potency of such compounds to trigger AR, dose-response curves for mGX and mGIIA were realized (FIG. 2B).

The "triggered rate" of AR corresponding to the total rate subtracted of the spontaneous AR has been plotted. mGX sPLA2 was a highly potent activator of AR since concentrations as low as 0.2 nM induced around 20% of AR above basal spontaneous level of AR. mGIIA was also a very potent activator of AR since 2 nM of enzyme induced around 20% of AR. mGIIA and mGX sPLA2 were thus able to induce AR on uncapacitated sperm. It is important to notice that increasing sPLA2 concentration from 20 to 200 nM did not produce a significant increase of the rate of acrosome-reacted sperm. A small part of sperm seems to be reluctant to sPLA2-induced AR (FIG. 2B).

b) sPLA2 was also been able to trigger AR on capacitated sperm.

Sperm were capacitated with 2% BSA in M16 medium, in a 5% CO2 incubator at 37° C. At 45 and 80 min, 200 nM of mGX was introduced in the capacitation medium and sperm were fixed 10 min later. The rates of acrosome-reacted sperm observed in the presence of sPLA2 were compared with control sperm capacitated during 55 or 90 min in the capacitation medium (FIG. 2C). In presence of sPLA2, the total rate of acrosome-reacted sperm increased at all capacitation durations in comparison to control condition. Moreover, the difference between spontaneous AR and total rate, corresponding to the sPLA2-induced fraction, was around stable throughout the capacitation progress: ≈39%, ≈36% and ≈35% at 10, 55 and 90 min respectively. It is important to notice that a small fraction of sperm of around 20% was reluctant to spontaneous AR or sPLA2-induced AR even in the presence of a high level of spontaneous AR.

Example 6

Determination of the Action Mode of sPLA2

It was essential to determine which action mode of sPLA2, enzymatic or via activation of a receptor, was involved in sPLA2-induced AR.

First, the mutated mGX was tested, with a substitution of one amino acid in the enzymatic pocket, H48Q.

FIG. 3 shows that the mutated mGX was unable to trigger AR of uncapacitated sperm (FIG. 3A).

Pro-mGX, the inactive precursor molecule was then tested. At a concentration of 200 nM, pro-mGX was also unable to trigger AR on uncapacitated sperm (FIG. 3A).

The specific sPLA2 inhibitor LY329722 at a dose of 1 µM blocks the ability of mGX to trigger acrosome reaction (FIG. 3B)

These results suggested that enzymatic activity played a crucial role in AR induced by sPLA2.

sPLA2 are calcium-dependent enzymes and are completely inactive in absence of calcium (Lambeau and Gelb, 2008) or in the presence of inhibitory divalent cations like $Ni^{2+}$ (Yu, B. Z., J. Rogers, G. R. Nicol, K. H. Theopold, K. Seshadri, S. Vishweshwara, and M. K. Jain. 1998. Catalytic significance of the specificity of divalent cations as KS* and kcat* cofactors for secreted phospholipase A2. Biochemistry. 37:12576-12587).

Calcium was removed from the sperm culture medium, and sPLA2, incubated at 200 nM during 10 min was unable to induce AR, contrary to a control experiment with 2 mM $Ca^{2+}$ in the culture medium (FIG. 3C). An identical result was obtained in the presence of 2 mM $Ni^{2+}$ in the culture medium (FIG. 3C).

Metabolites obtained downstream activation of sPLA2, that are lysophospholipids and unsaturated fatty acids, were known for decades to activate AR (Meizel, S. and K. O. Turner. 1983. Stimulation of an exocytotic event, the hamster sperm acrosome reaction, by cis-unsaturated fatty acids. FEBS Lett. 161:315-318.; Fleming, A. D. and R. Yanagimachi. 1984. Evidence suggesting the importance of fatty acids and the fatty acid moieties of sperm membrane phospholipids in the acrosome reaction of guinea pig spermatozoa. J. Exp. Zool. 229:485-489). From the studies realized, AR induced by sPLA2 metabolites required: i) 1 or 4 hours of incubation for lysophospholipids and unsaturated fatty acids respectively, ii) pretty high concentrations of metabolites around 100 µM, iii) capacitated sperm for activation by fatty acid.

Because mGX promoted AR at sub nanomolar concentrations in 10 min of incubation, we re-tested lysophospholipids and unsaturated fatty acids in different conditions than previously tested and closer to sPLA2 experiments: sperm were incubated with lower concentrations of around 10 µM of lysophospholipids and unsaturated fatty acids (LPC and arachidonic acid) and during 45 min during the capacitation or 4 h after gamete mixing.

In these conditions, arachidonic acid (fatty acid) and LPC (lysophospholipid) mimic mGX sPLA2 (FIG. 7).

Example 7

In Vitro Fertilization (IVF) Protocol

Sperm cells, obtained by manual trituration of caudae epididymes from OF1 male mice, were allowed to swim in M2 medium for 10 min. Then, the sperm cells were transferred in M16 medium containing 2% BSA (Bovine Serum Albumen) and incubated 35 min for capacitation. After centrifugation, cells were then transferred in M16 medium and if necessary, incubated with 20 or 200 nM of mGX sPLA2 for 10 min. Sperm cells were centrifugated (1200 rpm, 5 min) and resuspended in M16 medium to remove mOX sPLA2 before to be used for in vitro fertilization experiment. All experiments were carried out at 37° C. Eggs were collected from mature OF1 females (6-weeks old) synchronized with 7.5 units of PMSG (pregnant mare serum gonadotrophin) and 7.5 units of hCG (human chorionic gonadotrophin) before collection.

IVF using standard protocols were carried out. Eggs were incubated with approximately $10^4$ sperm cells, and unbound sperms were washed away after 4 hours of incubation. Twenty four hours after fertilization, the two-cell embryos stages (FIG. 4) were scored as an indication of successful fertilization (FIGS. 5 and 6).

Example 8

IVF with Sperm Treated with sPLA2 During 10 Minutes

In vitro fertilizations (IVF) were realized with sperm capacitated 35 min in 2% BSA and then treated 10 min with 20 or 200 nM mGX. Before treated sperm were introduced within oocytes, sperm were washed and centrifuged to remove sPLA2 in order to avoid artefact effects of sPLA2 on sperm-oocyte fusion (Riffo and Parraga, 1997). sPLA2 contaminant in the IVF medium was below 1 nM for sperm treated at 200 nM.

a) Evaluation of the number of intact acrosome sperm

At 200 nM mGX, between 70% and 80% of sperm have lost their acrosome.

b) Calculation of the IVF rate with normal and treated sperm

The rate of IVF with normal and treated sperm based on the number of oocytes reaching the 2-cells embryo stage at 24 hours has been calculated. The rate of IVF was increased in the presence of mGX sPLA2 in a dose-dependant way.

The mean IVF rate increased from 44.0±8.9% in control conditions to 65.4+5.6% for IVF realized with sperm treated with 200 nM sPLA2 (n=13 different males). Control and sPLA2 experiments have been performed simultaneously and a statistic analysis using paired t-test showed that the difference was highly statistically significant (p=0.0002) (FIG. 5A).

Example 9

Contraception Induced by sPLA2 from Animal Venom

The protocol use is the same as in example 7, except the use of sPLA2 liable to prevent said fertilization as defined above instead of a sPLA2 liable to increase said fertilization as defined above. At 20 nM and 200 nM, the taipan toxic sPLA2 OS2 inhibits IVF. (FIG. 6).

The invention claimed is:

1. A method for treating sterility, or for promoting or improving fertilization, or for promoting or improving a viable embryogenesis comprising the steps of: treating a sample comprising spermatozoa in vitro with a therapeutically effective amount of a mammalian group X secreted phospholipase A2 (group X sPLA2) to target inefficient spermatozoa and trigger an early acrosome reaction on said inefficient spermatozoa in the absence of oocytes, and contacting said group X sPLA2-treated spermatozoa sample with an oocyte having zona pellucida, wherein said in vitro treatment of spermatozoa results in enrichment of efficient spermatozoa and improved fertilization.

2. The method according to claim 1, wherein the method treats sterility, promotes or improves fertilization, or promotes or improves viable embryogenesis in a mammal.

3. The method according to claim 2, wherein the method treats a female mammal undergoing in vitro fertilization procedure (IVF), gamete intrafallopian transfer procedure (GIFT), intracytoplasmic sperm injection procedure (ICSI), or therapeutic donor insemination procedure (TDI) during assisted reproductive technologies (ART).

4. The method according to claim 2, wherein said group X sPLA2 hydrolyse hydrolyzes the sn-2 ester of one or more anionic and zwitterionic glycero-phospholipids with a specific activity of from about 1 μmol/min/mg to about 50 μmol/min/mg.

5. The method according to claim 2, wherein said group X sPLA2 hydrolyzes the sn-2 ester of one or more anionic and zwitterionic glycero-phospholipids with a specific activity of from about 1 μmol/min/mg to about 50 μmol/min/mg, wherein said glycero-phospholipids are selected from the group consisting of: 1-palmitoyl-2-oleoyl-sn-glycero-3-phosphoglycerol (POPG), 1-palmitoyl-2-oleoyl-sn-glycero-3-phosphocholine (POPC), and 1 palmitoyl-2-oleoyl-sn-glycero-3-phosphoserine (POPS).

6. The method according to claim 2, wherein said group X sPLA2 hydrolyzes the sn-2 ester of one or more anionic and zwitterionic glycero-phospholipids with a specific activity of from about 1 μmol/min/mg to about 50 μmol/min/mg and said glycerol phospholipids being selected from the group consisting of: 1-palmitoyl-2-oleoyl-sn-glycero-3-phosphoglycerol (POPG), 1-palmitoyl-2-oleoyl-sn-glycero-3-phosphocholine (POPC), and 1-palmitoyl-2-oleoyl-sn-glycero-3-phosphoserine (POPS), wherein the specific activity towards POPG is from about 1 to about 50 μmol/min/mg, and/or the specific activity towards POPC is from about 1 to about 25 μmol/min/mg, and/or the specific activity towards POPS is from about 1 to about 50 μmol/min/mg.

7. The method according to claim 2, wherein said group X sPLA2 is at a concentration from about 0.2 nM to about 200 nM.

* * * * *